United States Patent
Savory et al.

(10) Patent No.: US 11,040,969 B2
(45) Date of Patent: *Jun. 22, 2021

(54) COMPOUNDS I

(71) Applicant: BENEVOLENTAI CAMBRIDGE LIMITED, London (GB)

(72) Inventors: Edward Savory, Cambourne (GB); Michael Higginbottom, Caldecote (GB); Kathryn Oliver, Cambridge (GB); Viet-Anh Anne Horgan, Redhill (GB)

(73) Assignee: BENEVOLENTAI CAMBRIDGE LIMITED, London (GB)

( * ) Notice: Subject to any disclaimer, the term of this patent is extended or adjusted under 35 U.S.C. 154(b) by 0 days.

This patent is subject to a terminal disclaimer.

(21) Appl. No.: 16/514,413

(22) Filed: Jul. 17, 2019

(65) Prior Publication Data

US 2019/0359611 A1 Nov. 28, 2019

Related U.S. Application Data

(60) Continuation of application No. 15/858,407, filed on Dec. 29, 2017, now Pat. No. 10,399,973, which is a continuation of application No. 15/335,751, filed on Oct. 27, 2016, now Pat. No. 9,890,160, which is a continuation of application No. 14/684,813, filed on Apr. 13, 2015, now Pat. No. 9,493,457, which is a continuation of application No. 14/062,969, filed on Oct. 25, 2013, now Pat. No. 9,035,066, which is a continuation of application No. 13/567,146, filed on Aug. 6, 2012, now Pat. No. 8,569,338, which is a division of application No. 13/062,318, filed as application No. PCT/EP2009/062011 on Sep. 16, 2009, now Pat. No. 8,263,616.

(60) Provisional application No. 61/106,734, filed on Oct. 20, 2008.

(30) Foreign Application Priority Data

Sep. 16, 2008 (SE) .................................... 0801979-6

(51) Int. Cl.
*C07D 471/04* (2006.01)
*A61K 31/437* (2006.01)

(52) U.S. Cl.
CPC .......... *C07D 471/04* (2013.01); *A61K 31/437* (2013.01)

(58) Field of Classification Search
CPC ........................... C07D 471/04; A61K 31/437
See application file for complete search history.

(56) References Cited

U.S. PATENT DOCUMENTS

| | | |
|---|---|---|
| 4,141,899 A | 2/1979 | Arcari et al. |
| 4,223,146 A | 9/1980 | Arcari et al. |
| 6,908,926 B1 | 6/2005 | Doerwald et al. |
| 8,263,616 B2 | 9/2012 | Savory et al. |
| 8,569,338 B2 | 10/2013 | Savory et al. |
| 9,493,457 B2 | 11/2016 | Savory et al. |
| 9,890,160 B2 | 2/2018 | Savory et al. |
| 2002/0198189 A1 | 12/2002 | Besencon et al. |

FOREIGN PATENT DOCUMENTS

| | | |
|---|---|---|
| WO | WO 2002/038153 | 5/2002 |
| WO | WO 2010/031789 | 3/2010 |

OTHER PUBLICATIONS

Mar. 10, 2009 International-Type Search Report issued in priority application SE 0801979-6.
Arcari et al., "Anti-ulcer and Antisecretory Activity of Selected Imidazopiperidines", Arzneim.-Forsch./Drug Res. 34(11), Nr. II (1984), pp. 1467-1471.
Byrn, Solid State Chemistry of Drugs, 2nd edition. 1999, SSCI Inc, Chapter 10, Polymorphs, pp. 232-247.
Dunkel, "Semicarbazide-sensitive amine oxidase/vascular adhesion protein-1: a patent survey", 2011, Expert Opin. Ther. Patents, vol. 21, No. 9, pp. 1453-1471.
International Search Report, dated Nov. 2009.
Magyar, "Semicarbazide-sensitive amine oxidase—its physiological significance", 2001, Pure Appl. Chem, vol. 73, No. 9, pp. 1393-1400.

*Primary Examiner* — Karen Cheng
(74) *Attorney, Agent, or Firm* — Greenblum & Bernstein, P.L.C.

(57) ABSTRACT

The present invention relates to compounds of formula (I),

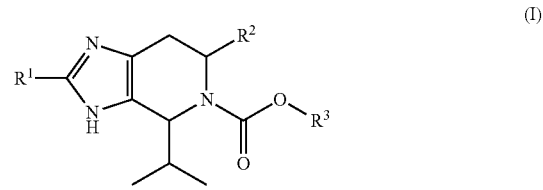

and their pharmaceutically acceptable salts, solvates, hydrates, geometrical isomers, tautomers, optical isomers or N-oxides, which are inhibitors of SSAO activity. The invention further relates to pharmaceutical compositions comprising these compounds and to the use of these compounds for the treatment of medical conditions wherein inhibition of SSAO activity is beneficial, such as inflammatory diseases and immune disorders.

6 Claims, No Drawings

COMPOUNDS I

CROSS-REFERENCE TO RELATED APPLICATIONS

This application is a Continuation of U.S. application Ser. No. 15/858,407 filed Dec. 29, 2017, which is a Continuation of U.S. application Ser. No. 15/335,751 filed Oct. 27, 2016, now U.S. Pat. No. 9,890,160, which is a Continuation of U.S. application Ser. No. 14/684,813 filed Apr. 13, 2015, now U.S. Pat. No. 9,493,457, which is a Continuation of U.S. application Ser. No. 14/062,969 filed Oct. 25, 2013, now U.S. Pat. No. 9,035,066, which is a Continuation of U.S. application Ser. No. 13/567,146 filed Aug. 6, 2012, now U.S. Pat. No. 8,569,338, which in turn is a Divisional of U.S. application Ser. No. 13/062,318 filed May 2, 2011, now U.S. Pat. No. 8,263,616, which in turn is a National Stage of PCT/EP2009/062011, filed Sep. 16, 2009, which claims Foreign Priority to Swedish App. No. 0801979-6, filed Sep. 16, 2008, and the benefit of U.S. Provisional App. No. 61/106,734, filed Oct. 20, 2008. Each application is incorporated by reference herein in its entirety.

FIELD OF THE INVENTION

The present invention relates to new 4,5,6,7-tetrahydroimidazo[4,5-c]pyridine compounds of formula (I), which are inhibitors of SSAO activity. The invention also relates to pharmaceutical compositions comprising these compounds and to the use of these compounds in the treatment or prevention of medical conditions wherein inhibition of SSAO activity is beneficial, such as inflammatory diseases and immune disorders.

BACKGROUND ART

Semicarbazide-sensitive amine oxidase (SSAO), otherwise known as Vascular Adhesion Protein-1 (VAP-1) or Amine Oxidase, Copper Containing 3 (AOC3), belongs to the copper-containing amine oxidase family of enzymes (EC. 1.4.3.6). Members of this enzyme family are sensitive to inhibition by semicarbazide and utilize cupric ion and protein-derived topa quinone (TPQ) cofactor in the oxidative deamination of primary amines to aldehydes, hydrogen peroxide, and ammonia according to the following reaction:

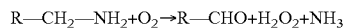

$R-CH_2-NH_2+O_2 \rightarrow R-CHO+H_2O_2+NH_3$

Known substrates for human SSAO include endogenous methylamine and aminoacetone as well as some xenobiotic amines such as benzylamine [Lyles, *Int. J. Biochem. Cell Biol.* 1996, 28, 259-274; Klinman, *Biochim. Biophys. Acta* 2003, 1647(1-2), 131-137; Mátyus et al., *Curr. Med. Chem.* 2004, 11(10), 1285-1298; O'Sullivan et al., *Neurotoxicology* 2004, 25(1-2), 303-315]. In analogy with other copper-containing amine oxidases, DNA-sequence analysis and structure determination suggest that the tissue-bound human SSAO is a homodimeric glycoprotein consisting of two 90-100 kDa subunits anchored to the plasma membrane by a single N-terminal membrane spanning domain [Morris et al., *J. Biol. Chem.* 1997, 272, 9388-9392; Smith et al., *J. Exp. Med.* 1998, 188, 17-27; Airenne et al., *Protein Science* 2005, 14, 1964-1974; Jakobsson et al., *Acta Crystallogr. D Biol. Crystallogr.* 2005, 61(Pt 11), 1550-1562].

SSAO activity has been found in a variety of tissues including vascular and non-vascular smooth muscle tissue, endothelium, and adipose tissue [Lewinsohn, *Braz. J. Med. Biol. Res.* 1984, 17, 223-256; Nakos & Gossrau, *Folia Histochem. Cytobiol.* 1994, 32, 3-10; Yu et al., *Biochem. Pharmacol.* 1994, 47, 1055-1059; Castillo et al., *Neurochem. Int.* 1998, 33, 415-423; Lyles & Pino, *J. Neural. Transm. Suppl.* 1998, 52, 239-250; Jaakkola et al., *Am. J. Pathol.* 1999, 155, 1953-1965; Morin et al., *J. Pharmacol. Exp. Ther.* 2001, 297, 563-572; Salmi & Jalkanen, *Trends Immunol.* 2001, 22, 211-216]. In addition, SSAO protein is found in blood plasma and this soluble form appears to have similar properties as the tissue-bound form [Yu et al., *Biochem. Pharmacol.* 1994, 47, 1055-1059; Kurkijairvi et al., *J. Immunol.* 1998, 161, 1549-1557]. It has recently been shown that circulating human and rodent SSAO originates from the tissue-bound form [Göktürk et al., *Am. J. Pathol.* 2003, 163(5), 1921-1928; Abella et al., *Diabetologia* 2004, 47(3), 429-438; Stolen et al., *Circ. Res.* 2004, 95(1), 50-57], whereas in other mammals the plasma/serum SSAO is also encoded by a separate gene called AOC4 [Schwelberger, *J. Neural. Transm.* 2007, 114(6), 757-762].

The precise physiological role of this abundant enzyme has yet to be fully determined, but it appears that SSAO and its reaction products may have several functions in cell signalling and regulation. For example, recent findings suggest that SSAO plays a role in both GLUT4-mediated glucose uptake [Enrique-Tarancon et al., *J. Biol. Chem.* 1998, 273, 8025-8032; Morin et al., *J. Pharmacol. Exp. Ther.* 2001, 297, 563-572] and adipocyte differentiation [Fontana et al., *Biochem. J.* 2001, 356, 769-777; Mercier et al., *Biochem. J.* 2001, 358, 335-342]. In addition, SSAO has been shown to be involved in inflammatory processes where it acts as an adhesion protein for leukocytes [Salmi & Jalkanen, *Trends Immnunol.* 2001, 22, 211-216; Salmi & Jalkanen, in "*Adhesion Molecules: Functions and Inhibition*" K. Ley (Ed.), 2007, pp. 237-251], and might also play a role in connective tissue matrix development and maintenance [Langford et al., *Cardiovasc. Toxicol.* 2002, 2(2), 141-150; Göktürk et al., *Am. J. Pathol.* 2003, 163(5), 1921-1928]. Moreover, a link between SSAO and angiogenesis has recently been discovered [Noda et al., *FASEB J.* 2008, 22(8), 2928-2935].

Several studies in humans have demonstrated that SSAO activity in blood plasma is elevated in conditions such as congestive heart failure, diabetes mellitus, Alzheimer's disease, and inflammation [Lewinsohn, *Braz. J. Med. Biol. Res.* 1984, 17, 223-256; Boomsma et al., *Cardiovasc. Res.* 1997, 33, 387-391; Ekblom, *Pharmacol. Res.* 1998, 37, 87-92; Kurkijairvi et al., *J. Immunol.* 1998, 161, 1549-1557; Boomsma et al., *Diabetologia* 1999, 42, 233-237; Meszaros et al., *Eur. J. Drug Metab. Pharmacokinet.* 1999, 24, 299-302; Yu et al., *Biochim. Biophys. Acta* 2003, 1647(1-2), 193-199; Mátyus et al., *Curr. Med. Chem.* 2004, 11(10), 1285-1298; O'Sullivan et al., *Neurotoxicology* 2004, 25(1-2), 303-315; del Mar Hernandez et al., *Neurosci. Lett.* 2005, 384(1-2), 183-187]. The mechanisms underlying these alterations of enzyme activity are not clear. It has been suggested that reactive aldehydes and hydrogen peroxide produced by endogenous amine oxidases contribute to the progression of cardiovascular diseases, diabetic complications and Alzheimer's disease [Callingham et al., *Prog. Brain Res.* 1995, 106, 305-321; Ekblom, *Pharmacol. Res.* 1998, 37, 87-92; Yu et al., *Biochim. Biophys. Acta* 2003, 1647(1-2), 193-199; Jiang et al., *Neuropathol Appl Neurobiol.* 2008, 34(2), 194-204]. Furthermore, the enzymatic activity of SSAO is involved in the leukocyte extravasation process at sites of inflammation where SSAO has been shown to be strongly expressed on the vascular endothelium [Salmi et al., *Immunity* 2001, 14(3), 265-276; Salmi & Jalkanen, in "*Adhesion Molecules: Functions and Inhibi-* tion" K. Ley (Ed.), 2007, pp. 237-251]. Accordingly, inhibition of SSAO has been suggested to have a therapeutic value in the prevention of diabetic complications and in inflammatory diseases [Ekblom, *Pharmacol. Res.* 1998, 37, 87-92; Salmi et al., *Immunity* 2001, 14(3), 265-276; Salter-Cid et al., *J. Pharmacol. Exp. Ther.* 2005, 315(2), 553-562].

SSAO knockout animals are phenotypically overtly normal but exhibit a marked decrease in the inflammatory responses evoked in response to various inflammatory stimuli [Stolen et al., *Immunity* 2005, 22(1), 105-115]. In addition, antagonism of its function in wild type animals in multiple animal models of human disease (e.g. carrageenan-induced paw inflammation, oxazolone-induced colitis, lipopolysaccharide-induced lung inflammation, collagen-induced arthritis, endotoxin-induced uveitis) by the use of antibodies and/or small molecules has been shown to be protective in decreasing the leukocyte infiltration, reducing the severity of the disease phenotype and reducing levels of inflammatory cytokines and chemokines [Kirton et al., *Eur. J. Immunol.* 2005, 35(11), 3119-3130; Salter-Cid et al., *J. Pharmacol. Exp. Ther.* 2005, 315(2), 553-562; McDonald et al., *Annual Reports in Medicinal Chemistry* 2007, 42, 229-243; Salmi & Jalkanen, in "*Adhesion Molecules: Functions and Inhibition*" K. Ley (Ed.), 2007, pp. 237-251; Noda et al., *FASEB J.* 2008 22(4), 1094-1103; Noda et al., *FASEB J.* 2008, 22(8), 2928-2935]. This anti-inflammatory protection seems to be afforded across a wide range of inflammatory models all with independent causative mechanisms, rather than being restricted to one particular disease or disease model. This would suggest that SSAO may be a key nodal point for the regulation of the inflammatory response, and it therefore seems likely that SSAO inhibitors may be effective anti-inflammatory drugs in a wide range of human diseases.

The invention described here relates to novel tetrahydroimidazo[4,5-c]pyridine derivatives as a new class of chemically distinct SSAO inhibitors with biological, pharmacological, and pharmacokinetic characteristics that make them suitable for use as prophylactic or therapeutic agents in a wide range of human inflammatory diseases and immune disorders. This therapeutic capacity is designed to block SSAO enzyme action, reducing the levels of pro-inflammatory enzyme products (aldehydes, hydrogen peroxide and ammonia) whilst also decreasing the adhesive capacity of immune cells and correspondingly their activation and final extra-vasation. Diseases where such an activity is expected to be therapeutically beneficial include all diseases where immune cells play a prominent role in the initiation, maintenance or resolution of the pathology, such as multiple sclerosis, arthritis and vasculitis.

WO 00/63208 discloses tetrahydroimidazo[4,5-c]pyridine derivatives with agonistic or antagonistic activity on the histamine H3 receptor for use in the treatment of eating disorders, obesity, diabetes and inflammation. EP 531874 shows tetrahydroimidazo[4,5-c]pyridine derivatives having angiotensin II inhibitory activity, which can be used as hypotensive agents. U.S. Pat. No. 5,091,390 describes tetrahydroimidazo-[4,5-c]pyridine-based angiotensin II receptor inhibitors that are useful for the treatment of CNS disorders. GB 2028798 relates to tetrahydroimidazo[4,5-c]pyridine derivatives for the preparation of antiulcer and anticholinergic compounds. WO 02/38153 discloses the use of certain tetrahydroimidazo[4,5-c]pyridine derivatives as inhibitors of SSAO for the treatment of diabetes and vascular complications.

DISCLOSURE OF THE INVENTION

It has surprisingly been discovered that the SSAO inhibitory activity of tetrahydroimidazo[4,5-c]pyridine derivatives is drastically increased by the presence of an isopropyl group in the 4-position of these compounds. Such compounds are therefore useful in the treatment or prevention of diseases in which inhibition of SSAO activity is beneficial. As such they are potentially useful for the treatment or prevention of inflammation, inflammatory diseases, immune or autoimmune disorders. Consequently, the invention relates to a compound of formula (I),

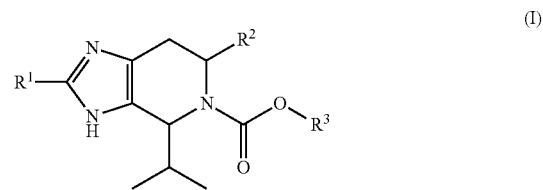

(I)

or a pharmaceutically acceptable salt, solvate, hydrate, geometrical isomer, tautomer, optical isomer or N-oxide thereof, wherein:
$R^1$ is selected from:
(a) hydrogen,
(b) $C_{1-6}$-alkyl, and
(c) —$NR^{4A}R^{4B}$;
$R^2$ is selected from:
(a) hydrogen,
(b) $C_{1-6}$-alkyl,
(c) halo-$C_{1-6}$-alkyl,
(d) hydroxy-$C_{1-6}$-alkyl,
(e) $C_{1-6}$-alkoxy-$C_{1-6}$-alkyl,
(f) halo-$C_{1-6}$-alkoxy-$C_{1-6}$-alkyl,
(g) $N(R^{4A}R^{4B})$—$C_{1-6}$-alkyl,
(h) —$C(O)NR^{4A}R^{4B}$, and
(i) —$C(O)O$—$C_{1-6}$-alkyl;
$R^3$ is selected from:
(a) $C_{1-6}$-alkyl,
(b) halo-$C_{1-6}$-alkyl,
(c) hydroxy-$C_{1-6}$-alkyl,
(d) $C_{1-6}$-alkoxy-$C_{1-6}$-alkyl,
(e) halo-$C_{1-6}$-alkoxy-$C_{1-6}$-alkyl,
(f) $N(R^{4A}R^{4B})$—$C_{1-6}$-alkyl,
(g) $C_{6-10}$-aryl-$C_{1-4}$-alkyl,
(h) heteroaryl-$C_{1-4}$-alkyl,
(i) $C_{6-10}$-aryloxy-$C_{1-4}$-alkyl,
(j) heteroaryloxy-$C_{1-4}$-alkyl,
(k) $C_{3-8}$-cycloalkyl,
(l) $C_{3-8}$-cycloalkyl-$C_{1-4}$-alkyl,
(m) heterocyclyl, and
(n) heterocyclyl-$C_{1-4}$-alkyl,
wherein any aryl or heteroaryl residue is optionally substituted with one or more substituents independently selected from halogen, hydroxy, cyano, nitro, $CF_3$, $C_{1-4}$-alkyl, $C_{1-4}$-alkoxy and —$NR^{4A}R^{4B}$, and wherein any cycloalkyl or heterocyclyl residue is optionally substituted with one or more substituents independently selected from halogen, hydroxy, $C_{1-4}$-alkyl, $C_{1-4}$-alkoxy and —$NR^{4A}R^{4B}$;
$R^{4A}$ and $R^{4B}$ are each independently selected from:
(a) hydrogen,
(b) $C_{1-6}$-alkyl, and
(c) $C_{1-6}$-acyl.
In a preferred embodiment of the invention, $R^1$ is H.
$R^2$ is preferably selected from hydrogen, —C(O)O—$C_{1-6}$-alkyl and —$C(O)NR^{4A}R^{4B}$.

More preferably, $R^2$ is selected from hydrogen, —C(O)O—$C_{1-3}$-alkyl and —C(O)NR$^{4A'}$R$^{4B'}$, wherein R$^{4A'}$ and R$^{4B'}$ are independently selected from hydrogen and $C_{1-2}$-alkyl.

In a most preferred embodiment, $R^2$ is hydrogen, —C(O)OMe, —C(O)NH$_2$ or —C(O)NHMe.

$R^3$ is preferably selected from halo-$C_{1-4}$-alkyl, halo-$C_{1-4}$-alkoxy-$C_{1-4}$-alkyl, di($C_{1-4}$-alkyl)amino-$C_{1-4}$-alkyl, $C_{6-10}$-aryl-$C_{1-4}$-alkyl, $C_{6-10}$-aryloxy-$C_{1-4}$-alkyl, heteroaryl-$C_{1-4}$-alkyl, heteroaryloxy-$C_{1-4}$-alkyl, heterocyclyl and heterocyclyl-$C_{1-4}$-alkyl, wherein any aryl, heteroaryl or heterocyclyl residue is optionally substituted with one or two substituents independently selected from halogen and $C_{1-4}$-alkyl.

More preferably, $R^3$ is selected from halo-$C_{1-2}$-alkyl, halo-$C_{1-2}$-alkoxy-$C_{1-2}$-alkyl, di($C_{1-2}$-alkyl)amino-$C_{1-2}$-alkyl, phenyl-$C_{1-2}$-alkyl, phenoxy-$C_{1-2}$-alkyl, $C_{5-6}$-heteroaryl-$C_{1-2}$-alkyl, $C_{5-6}$-heteroaryloxy-$C_{1-2}$-alkyl, heterocyclyl and heterocyclyl-$C_{1-2}$-alkyl, and wherein any phenyl, heteroaryl or heterocyclyl residue is optionally substituted with one or two substituents independently selected from halogen and $C_{1-2}$-alkyl.

In a most preferred embodiment, $R^3$ is 2,2,2-trichloroethyl, 2-chloro-2,2-difluoroethyl, 2,2,2-trifluoroethoxyethyl, dimethylaminoethyl, benzyl, pyridinylmethyl, pyrazinylmethyl, thiazolylmethyl, isoxazolylmethyl, phenoxyethyl, pyridinyloxyethyl, tetrahydrofuranyl, tetrahydrofuranylmethyl, pyrrolidinyl, pyrrolidinylmethyl or oxetanylmethyl, and wherein any phenyl, heteroaryl or heterocyclyl residue is optionally monosubstituted with halogen or methyl.

Specific preferred compounds of formula (I) are the compounds selected from the group consisting of:

2,2,2-Trichloroethyl 4-isopropyl-1,4,6,7-tetrahydro-5H-imidazo[4,5-c]pyridine-5-carboxylate;
2-Chloro-2,2-difluoroethyl 4-isopropyl-1,4,6,7-tetrahydro-5H-imidazo[4,5-c]pyridine-5-carboxylate;
Benzyl 4-isopropyl-1,4,6,7-tetrahydro-5H-imidazo[4,5-c]pyridine-5-carboxylate;
3-Chlorobenzyl 4-isopropyl-1,4,6,7-tetrahydro-5H-imidazo[4,5-c]pyridine-5-carboxylate;
4-Chlorobenzyl 4-isopropyl-1,4,6,7-tetrahydro-5H-imidazo[4,5-c]pyridine-5-carboxylate;
Pyridin-2-ylmethyl 4-isopropyl-1,4,6,7-tetrahydro-5H-imidazo[4,5-c]pyridine-5-carboxylate;
Pyridin-3-ylmethyl 4-isopropyl-1,4,6,7-tetrahydro-5H-imidazo[4,5-c]pyridine-5-carboxylate;
Pyridin-4-ylmethyl 4-isopropyl-1,4,6,7-tetrahydro-5H-imidazo[4,5-c]pyridine-5-carboxylate;
(5-Chloropyridin-2-yl)methyl 4-isopropyl-1,4,6,7-tetrahydro-5H-imidazo[4,5-c]pyridine-5-carboxylate;
Pyrazin-2-ylmethyl 4-isopropyl-1,4,6,7-tetrahydro-5H-imidazo[4,5-c]pyridine-5-carboxylate;
Benzyl (4S,6S)-6-(aminocarbonyl)-4-isopropyl-1,4,6,7-tetrahydro-5H-imidazo-[4,5-c]-pyridine-5-carboxylate;
Benzyl (4S,6S)-4-isopropyl-6-[(methylamino)carbonyl]-1,4,6,7-tetrahydro-5H-imidazo[4,5-c]pyridine-5-carboxylate;
5-Benzyl 6-methyl (4S,6S)-4-isopropyl-1,4,6,7-tetrahydro-5H-imidazo[4,5-c]pyridine-5,6-dicarboxylate;
2-Phenoxyethyl 4-isopropyl-1,4,6,7-tetrahydro-5H-imidazo[4,5-c]pyridine-5-carboxylate;
2-(4-Chlorophenoxy)ethyl 4-isopropyl-1,4,6,7-tetrahydro-5H-imidazo[4,5-c]pyridine-5-carboxylate;
(3S)-Tetrahydrofuran-3-yl (4S)-4-isopropyl-1,4,6,7-tetrahydro-5H-imidazo[4,5-c]pyridine-5-carboxylate;
Tetrahydrofuran-3-ylmethyl 4-isopropyl-1,4,6,7-tetrahydro-5H-imidazo[4,5-c]pyridine-5-carboxylate;
(3-Methyloxetan-3-yl)methyl 4-isopropyl-1,4,6,7-tetrahydro-5H-imidazo[4,5-c]pyridine-5-carboxylate;
2-(Dimethylamino)ethyl 4-isopropyl-1,4,6,7-tetrahydro-5H-imidazo[4,5-c]pyridine-5-carboxylate;
(2R)-Tetrahydrofuran-2-ylmethyl 4-isopropyl-1,4,6,7-tetrahydro-5H-imidazo[4,5-c]-pyridine-5-carboxylate;
1,3-Thiazol-2-ylmethyl 4-isopropyl-1,4,6,7-tetrahydro-5H-imidazo[4,5-c]pyridine-5-carboxylate;
(5-Methylisoxazol-3-yl)methyl 4-isopropyl-1,4,6,7-tetrahydro-5H-imidazo[4,5-c]pyridine-5-carboxylate;
[(2S)-1-Methylpyrrolidin-2-yl]methyl 4-isopropyl-1,4,6,7-tetrahydro-5H-imidazo-[4,5-c]-pyridine-5-carboxylate;
(3R)-1-methylpyrrolidin-3-yl 4-isopropyl-1,4,6,7-tetrahydro-5H-imidazo[4,5-c]pyridine-5-carboxylate;
Oxetan-2-ylmethyl 4-isopropyl-1,4,6,7-tetrahydro-5H-imidazo[4,5-c]pyridine-5-carboxylate;
2-(Pyridin-3-yloxy)ethyl 4-isopropyl-1,4,6,7-tetrahydro-5H-imidazo[4,5-c]pyridine-5-carboxylate; and
2-(2,2,2-Trifluoroethoxy)ethyl 4-isopropyl-1,4,6,7-tetrahydro-5H-imidazo[4,5-c]pyridine-5-carboxylate.

Another object of the present invention is a compound of formula (I) for use in therapy. The compounds as defined above are useful as inhibitors of SSAO activity. As such, they are useful in the treatment or prevention of conditions and diseases in which inhibition of SSAO activity is beneficial. More specifically, they are useful for the treatment or prevention of inflammation, inflammatory diseases, immune or autoimmune disorders.

In particular, it is believed that compounds of formula (I) are useful for the treatment or prevention of arthritis (such as rheumatoid arthritis, juvenile rheumatoid arthritis, osteoarthritis and psoriatic arthritis), synovitis, vasculitis, conditions associated with inflammation of the bowel (such as Crohn's disease, ulcerative colitis, inflammatory bowel disease and irritable bowel syndrome), atherosclerosis, multiple sclerosis, Alzheimer's disease, vascular dementia, pulmonary inflammatory diseases (such as asthma, chronic obstructive pulmonary disease and acute respiratory distress syndrome), fibrotic diseases (including idiopathic pulmonary fibrosis, cardiac fibrosis and systemic sclerosis (scleroderma)), inflammatory diseases of the skin (such as contact dermatitis, atopic dermatitis and psoriasis), systemic inflammatory response syndrome, sepsis, inflammatory and/or autoimmune conditions of the liver (such as autoimmune hepatitis, primary biliary cirrhosis, alcoholic liver disease, sclerosing cholangitis, and autoimmune cholangitis), diabetes (type I or II) and/or the complications thereof, chronic heart failure, congestive heart failure, ischemic diseases (such as stroke and ischemia-reperfusion injury), and myocardial infarction and/or the complications thereof.

It is believed that the compounds of the invention are especially useful for the treatment or prevention of vasculitis, including, but not limited to, giant cell arteritis, Takayasu's arteritis, Polyarteritis nodosa, Kawasaki disease, Wegener's granulomatosis, Churg-Strauss syndrome, microscopic polyangiitis, Henoch-Schönlein purpura, cryoglobulinemia, cutaneous leukocytoclastic angiitis and primary angiitis of the central nervous system.

The invention thus includes the use of said compounds in the manufacture of a medicament for the treatment or prevention of the above-mentioned conditions and diseases. The invention also includes methods for treatment or prevention of such conditions and diseases, comprising administering to a mammal, including man, in need of such treatment an effective amount of a compound as defined above.

Methods delineated herein include those wherein the subject is identified as in need of a particular stated treatment. Identifying a subject in need of such treatment can be in the judgment of a subject or a health care professional and can be subjective (e.g. opinion) or objective (e.g. measurable by a test or diagnostic method).

In other aspects, the methods herein include those further comprising monitoring subject response to the treatment administrations. Such monitoring may include periodic sampling of subject tissue, fluids, specimens, cells, proteins, chemical markers, genetic materials, etc. as markers or indicators of the treatment regimen. In other methods, the subject is pre-screened or identified as in need of such treatment by assessment for a relevant marker or indicator of suitability for such treatment.

In one embodiment, the invention provides a method of monitoring treatment progress. The method includes the step of determining a level of diagnostic marker (Marker) (e.g., any target or cell type delineated herein modulated by a compound herein) or diagnostic measurement (e.g., screen, assay) in a subject suffering from or susceptible to a disorder or symptoms thereof delineated herein, in which the subject has been administered a therapeutic amount of a compound herein sufficient to treat the disease or symptoms thereof. The level of Marker determined in the method can be compared to known levels of Marker in either healthy normal controls or in other afflicted patients to establish the subject's disease status. In preferred embodiments, a second level of Marker in the subject is determined at a time point later than the determination of the first level, and the two levels are compared to monitor the course of disease or the efficacy of the therapy. In certain preferred embodiments, a pre-treatment level of Marker in the subject is determined prior to beginning treatment according to this invention; this pre-treatment level of Marker can then be compared to the level of Marker in the subject after the treatment commences, to determine the efficacy of the treatment.

In certain method embodiments, a level of Marker or Marker activity in a subject is determined at least once. Comparison of Marker levels, e.g., to another measurement of Marker level obtained previously or subsequently from the same patient, another patient, or a normal subject, may be useful in determining whether therapy according to the invention is having the desired effect, and thereby permitting adjustment of dosage levels as appropriate. Determination of Marker levels may be performed using any suitable sampling/expression assay method known in the art or described herein. Preferably, a tissue or fluid sample is first removed from a subject. Examples of suitable samples include blood, urine, tissue, mouth or cheek cells, and hair samples containing roots. Other suitable samples would be known to the person skilled in the art. Determination of protein levels and/or mRNA levels (e.g., Marker levels) in the sample can be performed using any suitable technique known in the art, including, but not limited to, enzyme immunoassay, ELISA, radiolabeling/assay techniques, blotting/chemiluminescence methods, real-time PCR, and the like.

Definitions

The following definitions shall apply throughout the specification and the appended claims. Unless otherwise stated or indicated, the term "$C_{1-6}$-alkyl" denotes a straight or branched alkyl group having from 1 to 6 carbon atoms. For parts of the range "$C_{1-6}$-alkyl" all subgroups thereof are contemplated such as $C_{1-5}$-alkyl, $C_{1-4}$-alkyl, $C_{1-3}$-alkyl, $C_{1-2}$-alkyl, $C_{2-6}$-alkyl, $C_{2-5}$-alkyl, $C_{2-4}$-alkyl, $C_{2-3}$-alkyl, $C_{3-6}$-alkyl, $C_{4-5}$-alkyl, etc. Examples of said "$C_{1-6}$-alkyl" include methyl, ethyl, n-propyl, isopropyl, n-butyl, isobutyl, sec-butyl, t-butyl and straight- and branched-chain pentyl and hexyl.

Unless otherwise stated or indicated, the term "halo-$C_{1-6}$-alkyl" denotes a straight or branched $C_{1-6}$-alkyl group substituted by one or more halogen atoms. The term halo-$C_{1-6}$-alkyl includes fluoro-$C_{1-6}$-alkyl, chloro-$C_{1-6}$-alkyl, bromo-$C_{1-6}$-alkyl and iodo-$C_{1-6}$-alkyl. Examples of said halo-$C_{1-6}$-alkyl include 2-fluoroethyl, fluoromethyl, chloromethyl, trifluoromethyl, trichloromethyl, 2,2,2-trifluoroethyl, 2,2,2-trichloroethyl and 2-chloro-2,2-difluoroethyl.

Unless otherwise stated or indicated, the term "hydroxy-$C_{1-6}$-alkyl" denotes a straight or branched $C_{1-6}$-alkyl group that has a hydrogen atom thereof replaced with OH. Examples of said hydroxy-$C_{1-6}$-alkyl include hydroxymethyl, 2-hydroxyethyl, 2-hydroxypropyl and 2-hydroxy-2-methylpropyl.

The derived expression "$C_{1-6}$-alkoxy" is to be construed accordingly where a $C_{1-6}$-alkyl group is attached to the remainder of the molecule through an oxygen atom. For parts of the range "$C_{1-6}$-alkoxy" all subgroups thereof are contemplated such as $C_{1-5}$-alkoxy, $C_{1-4}$-alkoxy, $C_{1-3}$-alkoxy, $C_{1-2}$-alkoxy, $C_{2-6}$-alkoxy, $C_{2-5}$-alkoxy, $C_{2-4}$-alkoxy, $C_{2-3}$-alkoxy, $C_{3-6}$-alkoxy, $C_{4-5}$-alkoxy, etc. Examples of said "$C_{1-6}$-alkoxy" include methoxy, ethoxy, n-propoxy, isopropoxy, n-butoxy, isobutoxy, sec-butoxy, t-butoxy and straight- and branched-chain pentoxy and hexoxy etc.

Unless otherwise stated or indicated, the term "$C_{1-6}$-alkoxy-$C_{1-6}$-alkyl" refers to a straight or branched $C_{1-6}$-alkoxy group that is bonded to a straight or branched $C_{1-6}$-alkyl group via an oxygen atom of said $C_{1-6}$-alkoxy group. Representative examples of such groups include methoxymethyl and ethoxyethyl.

Unless otherwise stated or indicated, the term "halo-$C_{1-6}$-alkoxy-$C_{1-6}$-alkyl" refers to a $C_{1-6}$-alkoxy-$C_{1-6}$-alkyl group wherein the $C_{1-6}$-alkoxy group is substituted by one or more halogen atoms. Examples of said halo-$C_{1-6}$-alkoxy-$C_{1-6}$-alkyl include 2,2,2-trifluoroethoxyethyl and trifluoromethoxyethyl.

Unless otherwise stated or indicated, the term "$C_{1-6}$-acyl" denotes a carbonyl group that is attached through its carbon atom to a hydrogen atom (i.e., a formyl group) or to a straight or branched $C_{1-6}$-alkyl group, where alkyl is defined as above. For parts of the range "$C_{1-6}$-acyl" all subgroups thereof are contemplated such as $C_{1-5}$-acyl, $C_{1-4}$-acyl, $C_{1-3}$-acyl, $C_{1-2}$-acyl, $C_{2-6}$-acyl, $C_{2-5}$-acyl, $C_{2-4}$-acyl, $C_{2-3}$-acyl, $C_{3-6}$-acyl, $C_{4-5}$-acyl, etc. Exemplary acyl groups include formyl, acetyl, propanoyl, butanoyl, pentanoyl, hexanoyl.

Unless otherwise stated or indicated, the term "$C_{6-10}$-aryl" refers to a monocyclic or fused bicyclic hydrocarbon ring system comprising 6 to 10 ring atoms and wherein at least one ring is an aromatic ring. Examples of $C_{6-10}$-aryl groups are phenyl, indenyl, 2,3-dihydroindenyl (indanyl), 1-naphthyl, 2-naphthyl or 1,2,3,4-tetrahydronaphthyl.

Unless otherwise stated or indicated, the term "$C_{6-10}$-aryl-$C_{1-4}$-alkyl" refers to a $C_{6-10}$-aryl group that is directly linked to a straight or branched $C_{1-4}$-alkyl group. Examples of such groups include phenylmethyl (i.e., benzyl) and phenylethyl.

Unless otherwise stated or indicated, the term "$C_{6-10}$-aryloxy-$C_{1-4}$-alkyl" refers to a $C_{6-10}$-aryl group that is linked to a straight or branched $C_{1-4}$-alkyl group via a bridging oxygen atom.

Examples of such groups include phenoxymethyl and phenoxyethyl.

Unless otherwise stated or indicated, the term "heteroaryl" refers to a monocyclic or fused bicyclic heteroaromatic ring system comprising 5 to 10 ring atoms in which one or more of the ring atoms are other than carbon, such as nitrogen, sulphur or oxygen. Only one ring need to be aromatic and said heteroaryl moiety can be linked to the remainder of the molecule via a carbon or nitrogen atom in any ring. Examples of heteroaryl groups include furyl, pyrrolyl, thienyl, oxazolyl, isoxazolyl, imidazolyl, thiazolyl, isothiazolyl, pyridinyl, pyrimidinyl, tetrazolyl, quinazolinyl, indolyl, indolinyl, isoindolyl, isoindolinyl, pyrazolyl, pyridazinyl, pyrazinyl, quinolinyl, quinoxalinyl, thiadiazolyl, benzofuranyl, 2,3-dihydrobenzofuranyl, 1,3-benzodioxolyl, 1,4-benzodioxinyl, 2,3-dihydro-1,4-benzodioxinyl, benzothiazolyl, benzimidazolyl, benzothiadiazolyl, benzotriazolyl and chromanyl.

Unless otherwise stated or indicated, the term "heteroaryl-$C_{1-4}$-alkyl" refers to a heteroaryl group that is directly linked to a straight or branched $C_{1-4}$-alkyl group via a carbon or nitrogen atom of said ring system. Examples of such groups include pyridinylmethyl, pyrazinylmethyl, thiazolylmethyl and isoxazolylmethyl.

Unless otherwise stated or indicated, the term "heteroaryloxy-$C_{1-4}$-alkyl" refers to a heteroaryl group that is linked to a straight or branched $C_{1-4}$-alkyl group via a bridging oxygen atom.

Examples of such groups include pyridinyloxyethyl and pyrazinyloxymethyl.

Unless otherwise stated or indicated, the term "$C_{3-8}$-cycloalkyl" refers to a mono- or bicyclic, saturated or partially unsaturated hydrocarbon ring system having from 3 to 8 carbon atoms.

Bicyclic ring systems can be either fused or bridged. In a bridged cycloalkyl ring system, two non-adjacent carbon atoms of a monocyclic ring are linked by an alkylene bridge of between one and three additional carbon atoms. Examples of said $C_{3-8}$-cycloalkyl include cyclopropyl, cyclobutyl, cyclopentyl, cyclohexyl, cyclohexenyl, cycloheptyl, cycloheptenyl and cyclooctyl, as well as bicyclo[2.2.1]heptyl, bicyclo[2.2.2]octyl and bicyclo[3.2.1]octyl. For parts of the range "$C_{3-8}$-cycloalkyl" all subgroups thereof are contemplated such as $C_{3-7}$-cycloalkyl, $C_{3-6}$-cycloalkyl, $C_{3-5}$-cycloalkyl, $C_{3-4}$-cycloalkyl, $C_{4-8}$-cycloalkyl, $C_{4-7}$-cycloalkyl, $C_{4-6}$-cycloalkyl, $C_{4-8}$-cycloalkyl, $C_{5-8}$-cycloalkyl, $C_{5-7}$-cycloalkyl, $C_{5-6}$-cycloalkyl, $C_{6-8}$-cycloalkyl and $C_{6-7}$-cycloalkyl.

Unless otherwise stated or indicated, the term "$C_{3-8}$-cycloalkyl-$C_{1-4}$-alkyl" refers to a $C_{3-8}$-cycloalkyl group that is directly attached to a straight or branched $C_{1-4}$-alkyl group. Examples of $C_{3-8}$-cycloalkyl-$C_{1-4}$-alkyl groups include cyclopentylmethyl and cyclohexylethyl.

Unless otherwise stated or indicated, the term "heterocyclyl" or "heterocyclic ring" refers to a non-aromatic, fully saturated or partially unsaturated, preferably fully saturated, monocyclic ring system having 4 to 7 ring atoms with at least one heteroatom such as O, N, or S, and the remaining ring atoms are carbon. Examples of heterocyclic rings include piperidinyl, tetrahydropyranyl, tetrahydrofuranyl, oxetanyl, azepinyl, azetidinyl, pyrrolidinyl, morpholinyl, imidazolinyl, imidazolidinyl, thiomorpholinyl, pyranyl, dioxanyl, piperazinyl, homopiperazinyl and 5,6-dihydro-4H-1,3-oxazin-2-yl. When present, the sulfur atom may be in an oxidized form (i.e., S=O or O=S=O). Exemplary heterocyclic groups containing sulfur in oxidized form are 1,1-dioxido-thiomorpholinyl and 1,1-dioxido-isothiazolidinyl.

Unless otherwise stated or indicated, the term "heterocyclyl-$C_{1-4}$-alkyl" refers to a heterocyclic ring that is directly attached to a straight or branched $C_{1-4}$-alkyl group via a carbon or nitrogen atom of said ring system. Examples of heterocyclyl-$C_{1-4}$-alkyl groups include oxetanylmethyl, tetrahydrofuranylmethyl and pyrrolidinylmethyl.

"Halogen" refers to fluorine, chlorine, bromine or iodine.

"Hydroxy" refers to the —OH radical.

"Nitro" refers to the —$NO_2$ radical.

"Cyano" refers to the —CN radical.

"Optional" or "optionally" means that the subsequently described event or circumstance may but need not occur, and that the description includes instances where the event or circumstance occurs and instances in which it does not.

"Pharmaceutically acceptable" means being useful in preparing a pharmaceutical composition that is generally safe, non-toxic and neither biologically nor otherwise undesirable and includes being useful for veterinary use as well as human pharmaceutical use.

"Treatment" as used herein includes prophylaxis of the named disorder or condition, or amelioration or elimination of the disorder once it has been established.

"An effective amount" refers to an amount of a compound that confers a therapeutic effect on the treated subject. The therapeutic effect may be objective (i.e., measurable by some test or marker) or subjective (i.e., subject gives an indication of or feels an effect).

"Prodrugs" refers to compounds that may be converted under physiological conditions or by solvolysis to a biologically active compound of the invention. A prodrug may be inactive when administered to a subject in need thereof, but is converted in vivo to an active compound of the invention. Prodrugs are typically rapidly transformed in vivo to yield the parent compound of the invention, e.g. by hydrolysis in the blood. The prodrug compound usually offers advantages of solubility, tissue compatibility or delayed release in a mammalian organism (see Silverman, R. B., The Organic Chemistry of Drug Design and Drug Action, $2^{nd}$ Ed., Elsevier Academic Press (2004), pp. 498-549). Prodrugs of a compound of the invention may be prepared by modifying functional groups, such as a hydroxy, amino or mercapto groups, present in a compound of the invention in such a way that the modifications are cleaved, either in routine manipulation or in vivo, to the parent compound of the invention. Examples of prodrugs include, but are not limited to, acetate, formate and succinate derivatives of hydroxy functional groups or phenyl carbamate derivatives of amino functional groups.

Throughout the specification and the appended claims, a given chemical formula or name shall also encompass all salts, hydrates, solvates, N-oxides and prodrug forms thereof. Further, a given chemical formula or name shall encompass all tautomeric and stereoisomeric forms thereof. Stereoisomers include enantiomers and diastereomers. Enantiomers can be present in their pure forms, or as racemic (equal) or unequal mixtures of two enantiomers. Diastereomers can be present in their pure forms, or as mixtures of diastereomers. Diastereomers also include geometrical isomers, which can be present in their pure cis or trans forms or as mixtures of those.

The compounds of formula (I) may be used as such or, where appropriate, as pharmacologically acceptable salts (acid or base addition salts) thereof. The pharmacologically acceptable addition salts mentioned below are meant to comprise the therapeutically active non-toxic acid and base addition salt forms that the compounds are able to form. Compounds that have basic properties can be converted to their pharmaceutically acceptable acid addition salts by treating the base form with an appropriate acid. Exemplary acids include inorganic acids, such as hydrogen chloride, hydrogen bromide, hydrogen iodide, sulphuric acid, phosphoric acid; and organic acids such as formic acid, acetic acid, propanoic acid, hydroxyacetic acid, lactic acid, pyruvic acid, glycolic acid, maleic acid, malonic acid, oxalic acid, benzenesulphonic acid, toluenesulphonic acid, methanesulphonic acid, trifluoroacetic acid, fumaric acid, succinic acid, malic acid, tartaric acid, citric acid, salicylic acid, p-aminosalicylic acid, pamoic acid, benzoic acid, ascorbic acid and the like. Exemplary base addition salt forms are the sodium, potassium, calcium salts, and salts with pharmaceutically acceptable amines such as, for example, ammonia, alkylamines, benzathine, and amino acids, such as, e.g. arginine and lysine. The term addition salt as used herein also comprises solvates which the compounds and salts thereof are able to form, such as, for example, hydrates, alcoholates and the like.

Compositions For clinical use, the compounds of the invention are formulated into pharmaceutical formulations for various modes of administration. It will be appreciated that compounds of the invention may be administered together with a physiologically acceptable carrier, excipient, or diluent. The pharmaceutical compositions of the invention may be administered by any suitable route, preferably by oral, rectal, nasal, topical (including buccal and sublingual), sublingual, transdermal, intrathecal, transmucosal or parenteral (including subcutaneous, intramuscular, intravenous and intradermal) administration.

Other formulations may conveniently be presented in unit dosage form, e.g., tablets and sustained release capsules, and in liposomes, and may be prepared by any methods well known in the art of pharmacy. Pharmaceutical formulations are usually prepared by mixing the active substance, or a pharmaceutically acceptable salt thereof, with conventional pharmaceutically acceptable carriers, diluents or excipients. Examples of excipients are water, gelatin, gum arabicum, lactose, microcrystalline cellulose, starch, sodium starch glycolate, calcium hydrogen phosphate, magnesium stearate, talcum, colloidal silicon dioxide, and the like. Such formulations may also contain other pharmacologically active agents, and conventional additives, such as stabilizers, wetting agents, emulsifiers, flavouring agents, buffers, and the like. Usually, the amount of active compounds is between 0.1-95% by weight of the preparation, preferably between 0.2-20% by weight in preparations for parenteral use and more preferably between 1-50% by weight in preparations for oral administration.

The formulations can be further prepared by known methods such as granulation, compression, microencapsulation, spray coating, etc. The formulations may be prepared by conventional methods in the dosage form of tablets, capsules, granules, powders, syrups, suspensions, suppositories or injections. Liquid formulations may be prepared by dissolving or suspending the active substance in water or other suitable vehicles. Tablets and granules may be coated in a conventional manner. To maintain therapeutically effective plasma concentrations for extended periods of time, compounds of the invention may be incorporated into slow release formulations.

The dose level and frequency of dosage of the specific compound will vary depending on a variety of factors including the potency of the specific compound employed, the metabolic stability and length of action of that compound, the patient's age, body weight, general health, sex, diet, mode and time of administration, rate of excretion, drug combination, the severity of the condition to be treated, and the patient undergoing therapy. The daily dosage may, for example, range from about 0.001 mg to about 100 mg per kilo of body weight, administered singly or multiply in doses, e.g. from about 0.01 mg to about 25 mg each. Normally, such a dosage is given orally but parenteral administration may also be chosen.

Preparation of Compounds of the Invention

The compounds of formula (I) above may be prepared by, or in analogy with, conventional methods. The preparation of intermediates and compounds according to the examples of the present invention may in particular be illuminated by the following Scheme 1. Definitions of variables in the structures in schemes herein are commensurate with those of corresponding positions in the formulae delineated herein.

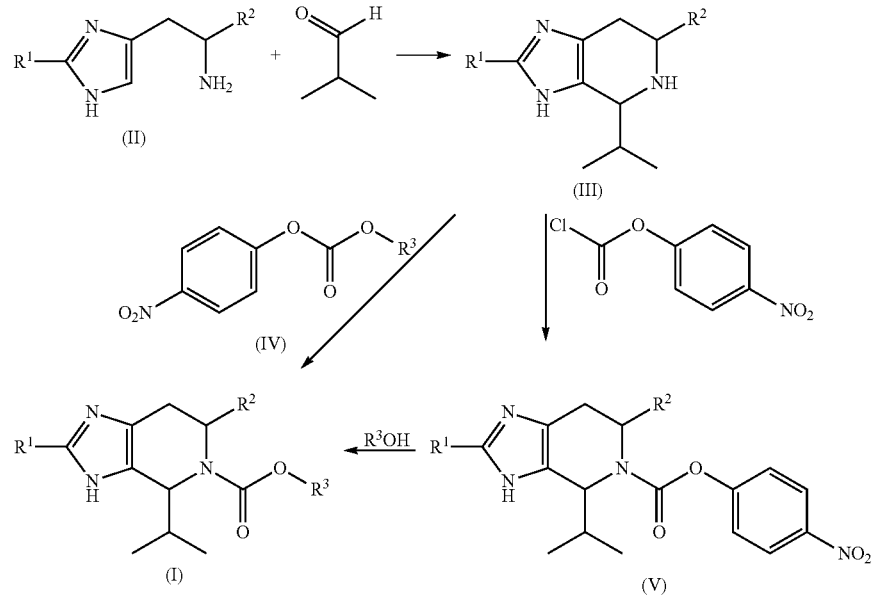

Scheme 1. General synthetic route for preparation of compounds of formula (I)

wherein $R^1$, $R^2$ and $R^3$ are as defined in formula (1).

A key intermediate in the synthesis of compounds of the invention is the 4-isopropyl-4,5,6,7-tetrahydro-1H-imidazo[4,5-c]pyridine derivative of formula (III), which can suitably be prepared by the condensation of the appropriate histamine derivative (II) with isobutyraldehyde. Compounds of formula (I) can then easily be obtained by installing the urethane linker containing $R^3$ onto this intermediate (III). Typically the urethane linkers incorporated into compounds of formula (I) have been synthesised utilising 4-nitrophenyl chloroformate as the activating agent, but other activating agents can also be used for this purpose. Such agents include, but are not limited to, e.g. phosgene to form alcohol chloroformates, or carbonyldiimidazole (CDI) to form imidazole carboylates.

In one process, the appropriate alcohol $R^3OH$ is activated by transformation into the corresponding 4-nitrophenyl carbonate derivative (IV). The intermediate (III) is then treated with this carbonate (IV) in the presence of a base (e.g., DIPEA, NMM or triethylamine) to give the desired compound of formula (I).

In another process, intermediate (III) is first transformed into its corresponding 4-nitrophenyl carbamate by treatment with 4-nitrophenyl chloroformate. The activated carbamate (V) is then subsequently treated with the appropriate alcohol $R^3OH$ to give the desired compound of formula (I).

The formation of the urethane functionality is typically a two step process but this may also be performed in a one-pot reaction by formation of the activated intermediate in situ. In such a process, the alcohol $R^3OH$ and 4-nitrophenyl chloroformate are first allowed to react in the presence of a base (e.g., DIPEA, NMM or triethylamine), after which intermediate (III) is added to the reaction mixture.

All of these alternatives are exemplified in the experimental section below.

Appropriate reaction conditions for the individual reaction steps are known to a person skilled in the art. Particular reaction conditions for examples of the invention are also described in the experimental section.

The necessary starting materials for preparing the compounds of formula (I) are either commercially available, or may be prepared methods known in the art.

The processes described below in the experimental section may be carried out to give a compound of the invention in the form of a free base or as an acid addition salt. A pharmaceutically acceptable acid addition salt may be obtained by dissolving the free base in a suitable organic solvent and treating the solution with an acid, in accordance with conventional procedures for preparing acid addition salts from base compounds. Examples of addition salt forming acids are mentioned above.

The compounds of formula (I) may possess one or more chiral carbon atoms, and they may therefore be obtained in the form of optical isomers, e.g., as a pure enantiomer, or as a mixture of enantiomers (racemate) or as a mixture containing diastereomers. The separation of mixtures of optical isomers to obtain pure enantiomers is well known in the art and may, for example, be achieved by fractional crystallization of salts with optically active (chiral) acids or by chromatographic separation on chiral columns.

The chemicals used in the synthetic routes delineated herein may include, for example, solvents, reagents, catalysts, and protecting group and deprotecting group reagents. Examples of protecting groups are t-butoxycarbonyl (Boc), benzyl and trityl (triphenylmethyl). The methods described above may also additionally include steps, either before or after the steps described specifically herein, to add or remove suitable protecting groups in order to ultimately allow synthesis of the compounds. In addition, various synthetic steps may be performed in an alternate sequence or order to give the desired compounds. Synthetic chemistry transformations and protecting group methodologies (protection and deprotection) useful in synthesizing applicable compounds are known in the art and include, for example, those described in R. Larock, *Comprehensive Organic Transformations*, VCH Publishers (1989); T. W. Greene and P. G. M. Wuts, *Protective Groups in Organic Synthesis*, 3$^{rd}$ Ed., John Wiley and Sons (1999); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995) and subsequent editions thereof.

The following abbreviations have been used:
Ac Acetate
Aq Aqueous
d Day
DCM Dichloromethane
DIPEA Diisopropylethylamine
DMAP Dimethylaminopyridine
DMF N,N'-Dimethylformamide
EDC 1-Ethyl-3-(3-dimethylaminopropyl)carbodiimide
ee Enantiomeric excess
ES$^+$ Electrospray
h Hour(s)
HBTU O-Benzotriazol-1-yl-N,N,N',N'-tetramethyluronium hexafluorophosphate
HOBt N-Hydroxybenzotriazole
HPLC High performance liquid chromatography
HRMS High resolution mass spectrometry
LCMS Liquid chromatography mass spectrometry
M Molar
[MH$^+$] Protonated molecular ion
min Minutes
NMM N-methyl morpholine
NMR Nuclear magnetic resonance
RP Reverse phase
MS Mass spectrometry
$R_T$ Retention time
sat Saturated
sec Seconds
THF Tetrahydrofuran
TFA Trifluoroacetic acid
TMS Tetramethylsilane The recitation of a listing of chemical groups in any definition of a variable herein includes definitions of that variable as any single group or combination of listed groups. The recitation of an embodiment herein includes that embodiment as any single embodiment or in combination with any other embodiments or portions thereof.

The invention will now be further illustrated by the following non-limiting examples. The specific examples below are to be construed as merely illustrative, and not limitative of the remainder of the disclosure in any way whatsoever. Without further elaboration, it is believed that one skilled in the art can, based on the description herein, utilize the present invention to its fullest extent. All references and publications cited herein are hereby incorporated by reference in their entirety.

EXAMPLES AND INTERMEDIATE COMPOUNDS

Experimental Methods

All reagents were commercial grade and were used as received without further purification, unless otherwise specified. Reagent grade solvents were used in all cases. 1H Nuclear magnetic resonance (NMR) was recorded on a Bruker DPX-400 spectrometer at 400 MHz. All spectra were recorded using residual solvent or tetramethylsilane (TMS) as internal standard. Analytical LCMS was performed on a Waters ZQ mass spectrometer connected to an Agilent 1100 HPLC system. Analytical HPLC was performed on an Agilent 1100 system. High-resolution mass spectra (HRMS) were obtained on an Agilent MSD-TOF connected to an Agilent 1100 HPLC system. During the analyses the calibration was checked by two masses and automatically corrected when needed. Spectra are acquired in positive electrospray mode. The acquired mass range was m/z 100-1100. Profile detection of the mass peaks was used. Flash chromatography was performed on either a CombiFlash Companion system equipped with RediSep silica columns or a Flash Master Personal system equipped with Strata SI-1 silica gigatubes. Reverse Phase HPLC was performed on a Gilson system (Gilson 322 pump with Gilson 321 equilibration pump and Gilson 215 autosampler) equipped with Phenomenex Synergi Hydro RP 150×10 mm, YMC ODS-A 100/150×20 mm or Chirobiotic T 250×10 mm columns. Reverse phase column chromatography was performed on a Gilson system (Gilson 321 pump and Gilson FC204 fraction collector) equipped with Merck LiChroprep® RP-18 (40-63 µm) silica columns. Microwave irradiations were carried out using a Biotage microwave. The compounds were automatically named using ACD 6.0. All compounds were dried in a vacuum oven overnight.

Analytical HPLC and LCMS data were obtained with:

System A: Phenomenex Synergi Hydro RP (C18, 30×4.6 mm, 4 µm), gradient 5-100% $CH_3CN$ (+0.085% TFA) in water (+0.1% TFA), 1.5 mL/min. with a gradient time of 1.75 min, 200 nm, 30° C.; or System B: Phenomenex Synergi Hydro RP (C18, 150×4.6 mm, 4 µm), gradient 5-100% $CH_3CN$ (+0.085% TFA) in water (+0.1% TFA), 1.5 mL/min with a gradient time of 7 min, 200 nm, 30° C.

Chiral HPLC data were obtained with:

System C: Chirobiotic V polar ionic mode (150×4.6 mm), 70% MeOH in 10 mM aq ammonium formate buffer, 1.0 mL/min, over 10 min, 200 nm, 30° C.

Intermediate 1

4-Isopropyl-4,5,6,7-tetrahydro-1H-imidazo[4,5-c]pyridine hydrochloride

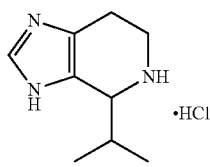

Histamine dihydrochloride (61.9 g, 336 mmol) was dissolved in a solution of NaOH (33.6 g, 841 mmol) in water (125 mL) and MeOH (500 mL), and isobutyraldehyde (61.4 mL, 672 mmol) was added. The reaction mixture was heated under reflux at 80° C. for 24 h, cooled to room temperature, the pH was adjusted to 7 with 1 M aq HCl solution (250 mL) and the solvents were removed in vacuo. The residue was dissolved in warm MeOH (300 mL), allowed to stand for 1 h, filtered and the solvents were removed in vacuo. The residue was stirred in MeOH (50 mL) and acetone (400 mL) for 2 h and was cooled to 4° C. for 2 h. The resulting precipitate was filtered and washed with acetone (100 mL) to give 4-isopropyl-4,5,6,7-tetrahydro-1H-imidazo[4,5-c]pyridine hydrochloride (33.0 g, 48.7%) as a white solid.

Analytical LCMS: purity>90% (System A, $R_T$=0.51 min), ES$^+$: 166.4 [MH]$^+$.

Intermediate 2

4-Nitrophenyl 4-isopropyl-1,4,6,7-tetrahydro-5H-imidazo[4,5-c]pyridine-5-carboxylate

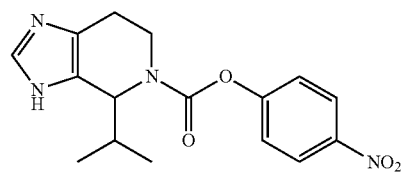 [SMILES: CC(C)C1c2[nH]cnc2CCN1C(=O)Oc1ccc([N+](=O)[O-])cc1]

Intermediate 1 (2.78 g, 8.28 mmol, 60% pure) and DIPEA (5.27 mL, 30.3 mmol) were dissolved in DCM (100 mL). The reaction mixture was cooled to 0° C. and 4-nitrophenyl chloroformate (4.07 g, 20.2 mmol) was added. The reaction mixture was stirred at room temperature for 18 h. The reaction mixture was washed with sat aq $NaHCO_3$ solution (5×100 mL), dried ($MgSO_4$) and the solvents were removed in vacuo to give 4-nitrophenyl 4-isopropyl-1,4,6,7-tetrahydro-5H-imidazo[4,5-c]pyridine-5-carboxylate (5.28 g, crude) as a yellow gum.

Analytical HPLC: purity 41% (System B, $R_T$=4.70 min); Analytical LCMS: purity 86% (System A, $R_T$=1.70 min), ES$^+$: 331.0 [MH]$^+$.

Intermediate 3

(4S,6S)-4-Isopropyl-4,5,6,7-tetrahydro-1H-imidazo[4,5-c]pyridine-6-carboxylic acid

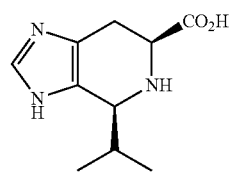

L-Histidine (10.0 g, 43.8 mmol) was dissolved in a solution of NaOH (7.73 g, 193 mmol) in water (25 mL) and MeOH (100 mL), and isobutyraldehyde (11.8 mL, 129 mmol) was added. The reaction mixture was heated under reflux at 80° C. for 24 h. The pH was adjusted to 7 with 1 M aq HCl solution and the solvents were removed in vacuo. The residue was dissolved in hot EtOH and cooled to room temperature. The precipitate was removed by filtration and the mother liquor concentrated in vacuo, washed with acetone (100 mL) and dried to give 4-isopropyl-4,5,6,7-tetrahydro-1H-imidazo[4,5-c]pyridine-6-carboxylic acid as a pale yellow solid (18.6 g, crude, 6:1 mixture of (4S,6S):(4R,6S) diastereoisomers).

1H NMR (400 MHz, CDCl$_3$) (diastereomers D1 and D2 observed in a 6:1 ratio): $\delta_H$ 3.96 (1H, m, D1), 3.93 (1H, br d, J 6.5 Hz, D2), 3.84 (1H, dd, J 8.2 and 5.3 Hz, D2), 3.49

(1H, dd, J 11.1 and 4.2 Hz, D1), 3.05 (1H, dd, J 15.8 and 5.3 Hz, D2), 3.01 (1H, ddd, J 15.4, 4.2 and 1.7 Hz, D1), 2.92 (1H, ddd, J 15.8, 8.2 and 0.9 Hz, D2), 2.72 (1H, ddd, J 15.4, 11.1 and 2.5 Hz, D1), 2.38 (1H, m, D1) and 2.19 (1H, m, D2).

The relative stereochemistry of the major diastereoisomer was determined to be cis by 1H NMR nOe experiments.

Intermediate 4

(4S,6S)-5-[(Benzyloxy)carbonyl]-4-isopropyl-4,5,6, 7-tetrahydro-1H-imidazo[4,5-c]-pyridine-6-carboxylic Acid

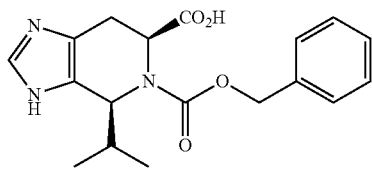 [SMILES: CC(C)[C@H]1c2[nH]cnc2C[C@@H](C(=O)O)N1C(=O)OCc1ccccc1]

Intermediate 3 (8.60 g, 47.8 mmol) was dissolved in Et$_2$O (25 mL) and 2 M aq NaOH solution (82 mL, 164 mmol) and the reaction mixture was cooled to 0° C. Benzyl chloroformate (12.9 mL, 90.4 mmol) was added and the reaction mixture was warmed to room temperature over 16 h. MeOH (50 mL) was added and the reaction mixture was stirred for 60 h. The pH was adjusted to 7 with 1 M aq HCl solution and the solvents were removed in vacuo. The residue was stirred in MeOH (50 mL) and the resulting white precipitate was removed by filtration. The solvents were removed in vacuo to give a crude orange gum (17.0 g). 11.0 g of this residue was stirred in hot EtOH/EtOAc, cooled and the resulting precipitate was removed by filtration. The solvents were removed in vacuo and the residue was purified by recrystallisation from hot MeOH/Et$_2$O to give (4S,6S)-5-[(benzyloxy)carbonyl]-4-isopropyl-4,5,6,7-tetrahydro-1H-imidazo [4,5-c]pyridine-6-carboxylic acid (2.50 g, 13.8%) as a white solid.

Analytical LCMS: purity>95% (System A, R$_T$=1.53 min), ES$^+$: 344.6 [MH]$^+$.

Example 1

2,2,2-Trichloroethyl 4-isopropyl-1,4,6,7-tetrahydro-5H-imidazo[4,5-c]pyridine-5-carboxylate

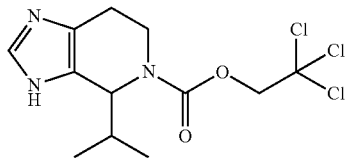 [SMILES: CC(C)C1c2[nH]cnc2CCN1C(=O)OCC(Cl)(Cl)Cl]

Intermediate 1 (2.33 g, 3.50 mmol, 45% pure) was suspended in DCM (20 mL) and DIPEA (1.83 mL, 10.5 mmol) and 2,2,2-trichloroethyl chloroformate (1.06 mL, 7.70 mmol) were added. The reaction mixture was stirred at room temperature for 16 h. The reaction mixture was partitioned between DCM (30 mL) and sat aq NaHCO$_3$ solution (20 mL). The organic layer was washed with sat aq NaHCO$_3$ solution (2×20 mL) and water (20 mL) and concentrated in vacuo. The residue was dissolved in MeOH (20 mL) and 1M aq NaOH solution (10 mL) was added. The reaction mixture was stirred for 1 h and the pH was adjusted to 7 with 1 M aq HCl solution and the solvents were removed in vacuo. The residue was partitioned between DCM (20 mL) and water (20 mL) and the organic layer was washed with water (20 mL), dried (MgSO$_4$) and concentrated in vacuo. The residue was purified by reverse phase HPLC (YMC ODS-A 100×20 mm, 5 μm, 25 mL/min, gradient 50% to 70% (over 7 min) then 100% (3 min) MeOH in 10% MeOH/water) to give 2,2,2-trichloroethyl 4-isopropyl-1,4,6,7-tetrahydro-5H-imidazo[4,5-c]pyridine-5-carboxylate (97 mg, 8%) as a white solid.

Analytical HPLC: purity 99.6% (System B, R$_T$=4.88 min); Analytical LCMS: purity 99.8% (System B, R$_T$=5.23 min), ES$^+$: 342.3 [MH]$^+$; HRMS calculated for C$_{12}$H$_{16}$Cl$_3$N$_3$O$_2$: 339.0308. found 339.0311.

Example 2

2-Chloro-2,2-difluoroethyl 4-isopropyl-1,4,6,7-tetrahydro-5H-imidazo[4,5-c]pyridine-5-carboxylate

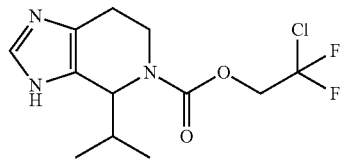 [SMILES: CC(C)C1c2[nH]cnc2CCN1C(=O)OCC(F)(F)Cl]

2-Chloro-2,2-difluoroethanol (1.69 g, 14.5 mmol) was dissolved in DCM (10 mL) at 0° C. and NMM (1.40 mL, 14.5 mmol) and 4-nitrophenyl chloroformate (2.93 g, 14.5 mmol) were added. The reaction mixture was stirred at room temperature for 5 h. A solution of Intermediate 1 (1.87 g, 2.97 mmol, 32% pure) and DIPEA (2.52 mL, 14.5 mmol) in DCM (20 mL) was added and the resulting solution was stirred for 2 d. The solvents were removed in vacuo, the residue was dissolved in MeOH (8 mL) and 1 M aq NaOH solution (6 mL) and the reaction mixture was stirred at room temperature for 18 h and concentrated in vacuo. The residue was dissolved in EtOAc (100 mL) and the organic layer was washed with 1M aq Na$_2$CO$_3$ solution (6×100 mL), dried (MgSO$_4$) and concentrated in vacuo. The residue was purified by column chromatography (normal phase, 20 g, Strata SI-1, silica gigatube, DCM (200 mL) followed by 2% and 4% MeOH in DCM (200 mL each)) and by reverse phase HPLC (YMC ODS-A 150×20 mm, 5 μm, 15 mL/min, isocratic run at 55% (over 12 min) then 100% (3 min) MeOH in 10% MeOH/water) to give 2-chloro-2,2-difluoroethyl 4-isopropyl-1,4,6,7-tetrahydro-5H-imidazo-[4,5-c] pyridine-5-carboxylate (13.0 mg, 1.4%) as a white solid.

Analytical HPLC: purity 99.0% (System B, R$_T$=4.47 min); Analytical LCMS: purity 100% (System B, R$_T$=4.95 min), ES$^+$: 308.0 [$^{35}$ClMH]$^+$ and 310.0 [$^{37}$ClMH]$^+$; HRMS calculated for C$_{12}$H$_{16}$ClF$_2$N$_3$O$_2$: 307.0899. found 307.0898.

Example 3

Benzyl 4-isopropyl-1,4,6,7-tetrahydro-5H-imidazo[4,5-c]pyridine-5-carboxylate

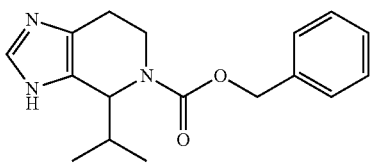 [SMILES: CC(C)C1c2[nH]cnc2CCN1C(=O)OCc1ccccc1]

Benzyl alcohol (0.88 g, 8.10 mmol) was dissolved in DCM (10 mL) and the reaction mixture was cooled to 0° C. NMM (0.89 mL, 8.10 mmol) and 4-nitrophenyl chloroformate (1.63 g, 8.10 mmol) were added and the reaction mixture was stirred at room temperature for 5 h. A solution of Intermediate 1 (1.16 g, 3.17 mmol, 55% pure) and DIPEA (2.69 mL, 15.4 mmol) in DCM (20 mL) was added and the resulting solution was stirred for 18 h. The solvents were removed in vacuo, the residue was dissolved in MeOH (10 mL) and 1 M aq NaOH solution (10 mL) and the reaction mixture was stirred for 2 h. The solvents were removed in vacuo, the residue was dissolved in EtOAc (120 mL), the organic layer was washed with 1 M aq $Na_2CO_3$ solution (4×100 mL), dried ($MgSO_4$) and the solvents were removed in vacuo. The residue was purified by column chromatography (normal phase, 20 g, Strata SI-1, silica gigatube, 0% to 5% MeOH in DCM), and by reverse phase HPLC (YMC ODS-A 100×20 mm, 5 μm, 25 mL/min, gradient 40% to 100% (over 7 min) then 100% (3 min) MeOH in 10% MeOH/water and YMC ODS-A 100×20 mm, 5 μm, 25 mL/min, gradient 0% to 100% (over 7 min) then 100% (3 min) MeOH in 10% MeOH/water to give benzyl 4-isopropyl-1,4,6,7-tetrahydro-5H-imidazo[4,5-c]pyridine-5-carboxylate (65.8 mg, 6.9%) as a white solid.

Analytical HPLC: purity 100% (System B, $R_T$=4.74 min); Analytical LCMS: purity 100% (System B. $R_T$=4.99 min), ES$^+$: 300.0 [MH]$^+$; HRMS calculated for $C_{17}H_{21}N_3O_2$: 299.1634. found 299.1636.

Example 4

3-Chlorobenzyl 4-isopropyl-1,4,6,7-tetrahydro-5H-imidazo[4,5-c]pyridine-5-carboxylate

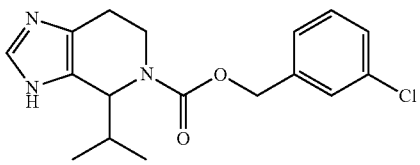 [SMILES: CC(C)C1c2[nH]cnc2CCN1C(=O)OCc1cccc(Cl)c1]

Carbonic acid 3-chloro-benzyl ester 4-nitro-phenyl ester (1.34 g, 4.40 mmol) was dissolved in DCM (10 mL) and cooled to 0° C. A solution of Intermediate 1 (1.00 g, 1.79 mmol, 36% pure) and DIPEA (0.70 mL, 6.60 mmol) in DCM (10 mL) was added and the reaction mixture was stirred at room temperature for 16 h. The solvent was removed in vacuo and the residue was dissolved in MeOH (8 mL) and 1M aq NaOH solution (6 mL) and stirred at room temperature for 2 h. The solvents were removed in vacuo and the residue was dissolved in EtOAc. The organic layer was washed with 1M aq $Na_2CO_3$ solution (8×50 mL), dried ($MgSO_4$) and concentrated in vacuo. The residue was purified by reverse phase HPLC (YMC ODS-A 100×20 mm, 5 μm, 25 mL/min, gradient 40% to 100% (over 7 min) then 100% (3 min) MeOH in 10% MeOH/water) to give 3-chlorobenzyl 4-isopropyl-1,4,6,7-tetrahydro-5H-imidazo[4,5-c]pyridine-5-carboxylate (116 mg, 19.5%) as a colourless gum.

Analytical HPLC: purity 98.8% (System B, $R_T$=5.06 min); Analytical LCMS: purity 100% (System B, $R_T$=5.47 min), ES$^+$: 334.0 [MH]$^+$; HRMS calculated for $C_{17}H_{20}ClN_3O_2$: 333.1244. found 333.1252.

Example 5

4-Chlorobenzyl 4-isopropyl-1,4,6,7-tetrahydro-5H-imidazo[4,5-c]pyridine-5-carboxylate

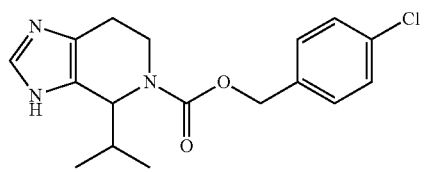 [SMILES: CC(C)C1c2[nH]cnc2CCN1C(=O)OCc1ccc(Cl)cc1]

(4-Chloro-phenyl)-methanol (0.51 g, 3.60 mmol) was suspended in DCM (10 mL) and NMM (0.35 mL, 3.60 mmol) and 4-nitrophenyl chloroformate (0.73 g, 3.6 mmol) were added at 0° C. The reaction was stirred at room temperature for 16 h. A solution of Intermediate 1 (500 mg, 1.49 mmol, 60% pure) and DIPEA (940 μL, 5.40 mmol) in DCM (10 mL) was added and the resulting solution was stirred at room temperature for 15 h. The solvents were removed in vacuo. The residue was dissolved in MeOH (8 mL) and 1 M aq NaOH solution (6 mL) and the reaction mixture was stirred for 2 h and concentrated in vacuo. The residue was dissolved in EtOAc (100 mL) and the organic layer washed with 1 M aq $Na_2CO_3$ solution (6×50 mL), brine (2×50 mL), dried ($MgSO_4$) and the solvents removed in vacuo. The residue was purified by reverse phase HPLC (YMC ODS-A 100×20 mm, 5 μm, 25 mL/min, gradient 50% to 80% (over 7 min) then 100% (3 min) MeOH in 10% MeOH/water) to give 4-chlorobenzyl 4-isopropyl-1,4,6,7-tetrahydro-5H-imidazo[4,5-c]pyridine-5-carboxylate (29.5 mg, 5.9%) as a colourless gum.

Analytical HPLC: purity 98.6% (System B, $R_T$=5.14 min); Analytical LCMS: purity 100% (System B, $R_T$=5.49 min), ES$^+$: 334.0 [MH]$^+$; HRMS calculated for $C_{17}H_{20}ClN_3O_2$: 333.1244. found 333.1237.

Example 6

Pyridin-2-ylmethyl 4-isopropyl-1,4,6,7-tetrahydro-5H-imidazo[4,5-c]pyridine-5-carboxylate

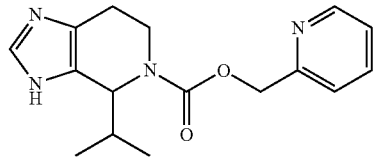

NaH (0.22 g, 5.0 mmol, 60% dispersion in mineral oil) was suspended in anhydrous THF (15 mL), the suspension was cooled to 0° C. and 2-pyridylmethanol (0.55 g, 5.0 mmol) was added. The suspension was stirred at 0° C. for 1 h and added to a stirred solution of Intermediate 2 (0.66 g, 2.00 mmol, 70% pure) in THF (10 mL) and the reaction mixture was stirred at room temperature. Two additional such portions of NaH and 2-pyridylmethanol in THF were added after 18 and 36 h, respectively. After 54 h the reaction mixture was quenched with water (10 mL), the solvents were removed in vacuo and the residue was dissolved in EtOAc (100 mL), washed with 1 M aq $Na_2CO_3$ solution (4×100 mL), dried ($MgSO_4$) and the solvents were removed in vacuo. The residue was purified by column chromatography (normal phase, 20 g, Strata SI-1, silica gigatube, DCM (200 mL) followed by 1%, 2% and 5% MeOH in DCM (200 mL each)) and reverse phase HPLC (Phenomenex Synergi, RP-Hydro 150×10 mm, 10 µm, 15 mL/min, gradient 0% to 70% (over 12 min) to 100% (over 3 min) MeOH in water (1% formic acid)). The residue was de-salted using $K_2CO_3$ in DCM to give pyridin-2-ylmethyl 4-isopropyl-1,4,6,7-tetrahydro-5H-imidazo[4,5-c]pyridine-5-carboxylate (86.4 mg, 14.4%) as a white solid. Analytical HPLC: purity 100% (System B, $R_T$=3.16 min); Analytical LCMS: purity 97.9% (System B, $R_T$=3.55 min), ES+: 301.1 [MH]+; HRMS calculated for $C_{16}H_{20}N_4O_2$: 300.1586. found 300.1581.

Example 7

Pyridin-3-ylmethyl 4-isopropyl-1,4,6,7-tetrahydro-5H-imidazo[4,5-c]pyridine-5-carboxylate

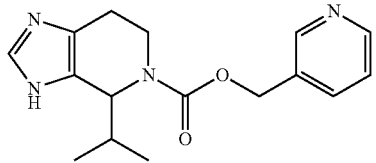 [SMILES: CC(C)C1c2[nH]cnc2CCN1C(=O)OCc1cccnc1]

NaH (0.19 g, 4.80 mmol, 60% dispersion in mineral oil) was suspended in anhydrous THF (5 mL), the suspension cooled to 0° C. and 3-pyridylcarbinol (0.40 mL, 4.00 mmol) was added. The suspension was stirred at 0° C. for 30 min and then added to a solution of Intermediate 2 (1.33 g, 4.00 mmol, 70% pure) in THF (10 mL) and the reaction mixture was stirred at room temperature. Two additional such portions of NaH and 3-pyridylcarbinol in THF were added after 7 and 25 h, respectively. After 4 d the reaction mixture was quenched with water (10 mL) and the solvents were removed in vacuo. The residue was dissolved in EtOAc (100 mL) washed with 1 M aq $Na_2CO_3$ solution (4×100 mL), dried ($MgSO_4$) and the solvents were removed in vacuo. The residue was purified by column chromatography (normal phase, 20 g, Strata SI-1, silica gigatube, DCM (200 mL) followed by 2%, 4%, 5% and 10% MeOH in DCM (200 mL each)) and reverse phase HPLC (Phenomenex Synergi, RP-Hydro 150×10 mm, 10 m, 15 mL/min, gradient 0% to 80% (over 12 min) to 100% (over 3 min) MeOH in water (1% formic acid) and Phenomenex Synergi, RP-Hydro 150×10 mm, 10 µm, 15 mL/min, gradient 0% to 40% (over 12 min) to 100% (over 3 min) MeOH in water (1% formic acid)). The residue was de-salted using $K_2CO_3$ in DCM to give pyridin-3-ylmethyl 4-isopropyl-1,4,6,7-tetrahydro-5H-imidazo[4,5-c]pyridine-5-carboxylate (46.3 mg, 3.8%) as a white solid.

Analytical HPLC: purity 100% (System B, $R_T$=3.07 min); Analytical LCMS: purity 99% (System B, $R_T$=3.07 min), ES+: 301.6; HRMS calculated for $C_{16}H_{20}N_4O_2$: 300.1586. found 300.1579.

Example 8

Pyridin-4-ylmethyl 4-isopropyl-1,4,6,7-tetrahydro-5H-imidazo[4,5-c]pyridine-5-carboxylate

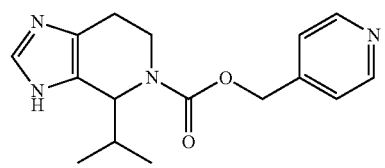 [SMILES: CC(C)C1c2[nH]cnc2CCN1C(=O)OCc1ccncc1]

Intermediate 1 (476 mg, 1.65 mmol, 70% pure) and DIPEA (1.39 mL, 8.00 mmol) were dissolved in DMF (20 mL) and carbonic acid 4-nitro-phenyl ester pyridin-4-ylmethyl ester (1.10 g, 4.00 mmol) was added. The reaction mixture was stirred at room temperature for 20 h and the solvents were removed in vacuo. The residue was dissolved in MeOH (10 mL) and 1 M aq NaOH solution (3 mL) was added. The reaction mixture was stirred at room temperature for 1 h and the solvents were removed in vacuo. The residue was dissolved in DCM (40 mL) and washed with 1 M aq $Na_2CO_3$ solution (5×40 mL). The organic layer was dried ($MgSO_4$) and the solvents were removed in vacuo. The residue was purified by reverse phase column chromatography (LiChroprep RP-18, 40-63 µm, 460×26 mm (100 g), 30 mL per min, gradient 0% to 100% (over 35 min) MeOH in water and LiChroprep RP-18, 40-63 µm, 460×26 mm (100 g), 30 mL per min, gradient 50% to 100% (over 35 min) MeOH in water) and reverse phase HPLC (YMC ODS-A 150×20 mm, 5 µm, 15 mL/min, gradient 0% to 50% (over 12 min) then 100% (3 min) MeOH in 10% MeOH/water) to give pyridin-4-ylmethyl 4-isopropyl-1,4,6,7-tetrahydro-5H-imidazo[4,5-c]pyridine-5-carboxylate (82 mg, 16.5%) as a white solid. Analytical HPLC: purity 100% (System B, $R_T$=3.05 min); Analytical LCMS: purity 100% (System B, $R_T$=3.42 min), ES+: 301.1 [MH]+; HRMS calculated for $C_{16}H_{20}N_4O_2$: 300.1586. found 300.1568.

Example 9

(5-Chloropyridin-2-yl)methyl 4-isopropyl-1,4,6,7-tetrahydro-5H-imidazo[4,5-c]pyridine-5-carboxylate

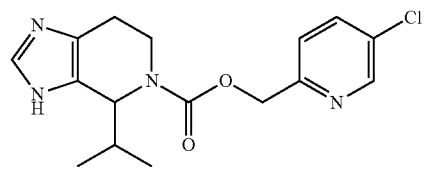

5-Chloropyridine-2-carboxylic acid (2.00 g, 12.7 mmol) was dissolved in THF (12 mL) at 0° C. and added to a solution of borane-THF (19.0 mL, 1 M in THF, 19.0 mmol).

THF (10 mL) was added and the reaction mixture was warmed to room temperature, stirred for 2 h and heated under reflux at 70° C. for 3 h. The reaction mixture was cooled to 0° C., quenched with aq 6 M HCl solution (4 mL) and the solution was stirred for 2 h and concentrated in vacuo. The residue was partitioned between H$_2$O (75 mL) and DCM (75 mL). The aq layer was washed with DCM (3×75 mL), adjusted to pH 9 with 4 M aq NaOH (3 mL) and extracted with DCM (3×75 mL). The organic layers were combined, dried (MgSO$_4$) and concentrated in vacuo to give 5-chloropyridine-2-methanol (0.83 g, 45%) as a brown gum.

Analytical HPLC: purity 79.5% (System B, R$_T$=3.04 min); Analytical LCMS: purity 85% (System A, R$_T$=1.15 min), ES$^+$: 143.97 [$^{35}$ClMH]$^+$ and 145.98 [MH$^{37}$Cl]$^+$.

NaH (80.0 mg, 2.00 mmol, 60% dispersion in mineral oil) was suspended in THF (10 mL), the suspension was cooled to 0° C. and 5-chloropyridine-2-methanol (0.29 g, 2.00 mmol) was added. The suspension was stirred at 0° C. for 30 min then added to a solution of Intermediate 2 (0.65 g, 2.00 mmol, 70% pure) in THF (10 mL) and the reaction mixture was stirred at room temperature. Two additional such portions of NaH and 5-chloropyridine-2-methanol in THF were added after 2 and 3 d, respectively. After 4 d the reaction mixture was quenched with water (10 mL) and the solvents were removed in vacuo. The solvents were removed in vacuo and the residue was dissolved in EtOAc (100 mL) washed with 1 M aq Na$_2$CO$_3$ solution (4×100 mL), dried (MgSO$_4$) and the solvents were removed in vacuo. The residue was purified by column chromatography (normal phase, 20 g, Strata SI-1, silica gigatube, DCM (200 mL) followed by 2%, 4%, 5% and 10% MeOH in DCM (200 mL each)) and reverse phase HPLC (Phenomenex Synergi, RP-Hydro 150×10 mm, 10 μm, 15 mL/min, gradient 20% to 80% (over 12 min) to 100% (over 3 min) MeOH in water (1% formic acid)). The residue was de-salted using K$_2$CO$_3$ to give (5-chloropyridin-2-yl)methyl 4-isopropyl-1,4,6,7-tetrahydro-5H-imidazo[4,5-c]pyridine-5-carboxylate (7.91 mg, 1.2%) as a white solid.

Analytical HPLC: purity 99.2% (System B, R$_T$=4.40 min); Analytical LCMS: purity 100% (System B, R$_T$=4.25 min), ES$^+$: 335.10 [$^{35}$ClMH]$^+$ and 337.10 [MH$^{37}$C$_1$]$^+$; HRMS calculated for C$_{16}$H$_{19}$ClN$_4$O$_2$: 334.1197. found 334.1189.

Example 10

Pyrazin-2-ylmethyl 4-isopropyl-1,4,6,7-tetrahydro-5H-imidazo[4,5-c]pyridine-5-carboxylate

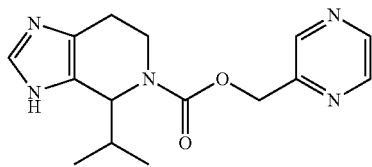

NaH (0.22 g, 5.60 mmol, 60% dispersion in mineral oil) was suspended in THF (10 mL), cooled to 0° C. and pyrazin-2-yl methanol (0.49 mL, 5.00 mmol) was added. The suspension was stirred at 0° C. for 30 min and then added to a solution of Intermediate 2 (0.66 g, 2.00 mmol, 70% pure) in THF (10 mL) and the reaction mixture was stirred at room temperature. An additional such portion of NaH and pyrazin-2-yl methanol in THF was added after 18 h. After 2 d the reaction mixture was quenched with water (10 mL) and the solvents were removed in vacuo. The residue was dissolved in MeOH (10 mL) and 1 M aq NaOH solution (10 mL) and the reaction mixture was stirred at room temperature for 2 h then concentrated in vacuo. The residue was dissolved in EtOAc (120 mL) and the organic layer was washed with 1 M aq Na$_2$CO$_3$ solution (6×100 mL), dried (MgSO$_4$) and the solvents were removed in vacuo. The residue was purified by reverse phase HPLC (Phenomenex Synergi, RP-Hydro 150×10 mm, 10 μm, 15 mL/min, gradient 0% to 100% (over 12 min) then 100% (over 3 min) MeOH in water (1% formic acid)). The residue was de-salted using K$_2$CO$_3$ in DCM to give pyrazin-2-ylmethyl 4-isopropyl-1,4,6,7-tetrahydro-5H-imidazo[4,5-c] pyridine-5-carboxylate (62.9 mg, 10.4%) as a white solid. Analytical HPLC: purity 99.2% (System B, R$_T$=3.59 min); Analytical LCMS: purity 100% (System B, R$_T$=3.99 min), ES$^+$: 302.1 [MH]$^+$; HRMS calculated for C$_{15}$H$_{19}$N$_5$O$_2$: 301.1539. found 301.1527.

Example 11

Benzyl (4S,6S)-6-(aminocarbonyl)-4-isopropyl-1,4,6,7-tetrahydro-5H-imidazo[4,5-c]-pyridine-5-carboxylate

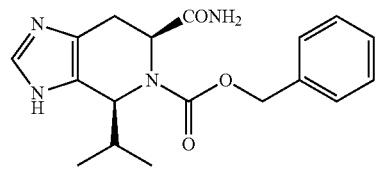 [SMILES: CC(C)[C@H]1c2[nH]cnc2C[C@@H](C(N)=O)N1C(=O)OCc1ccccc1]

Intermediate 4 (572 mg, 1.67 mmol) and ammonium chloride (178 mg, 3.33 mmol) were dissolved in DMF (5 mL), and DIPEA (1.16 mL, 6.66 mmol), HOBt (338 mg, 2.50 mmol) and HBTU (948 mg, 2.50 mmol) were added. The reaction mixture was stirred at room temperature for 3 d and concentrated in vacuo. The residue was partitioned between EtOAc (100 mL) and sat aq NaHCO$_3$ solution (80 mL). The organic layer was washed with sat aq NaHCO$_3$ solution (80 mL), dried (MgSO$_4$) and concentrated in vacuo. The residue was purified by column chromatography (normal phase, 20 g, Strata SI-1, silica gigatube, DCM (200 mL) followed by 2%, 4%, 5% and 10% MeOH in DCM (200 mL each) and reverse phase HPLC (YMC ODS-A 100×20 mm, 5 μm, 25 mL/min, gradient 40% to 70% (over 7 min) then 100% (3 min) MeOH in 10% MeOH/water) to give benzyl (4S,6S)-6-(aminocarbonyl)-4-isopropyl-1,4,6,7-tetrahydro-5H-imidazo[4,5-c]pyridine-5-carboxylate (163 mg, 28.7%) as a white solid.

Analytical HPLC: purity 99.4% (System B, R$_T$=4.20 min); Analytical LCMS: purity 100% (System B, R$_T$=4.13 min), ES$^+$: 343.7 [MH]$^+$; HRMS calcd for C$_{18}$H$_{22}$N$_4$O$_3$: 342.1692. found 342.1683.

Example 12

Benzyl (4S,6S)-4-isopropyl-6-[(methylamino)carbonyl]-1,4,6,7-tetrahydro-5H-imidazo[4,5-c]pyridine-5-carboxylate

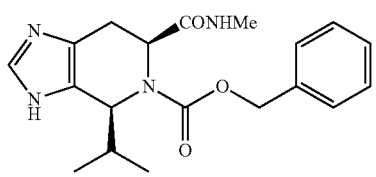

Intermediate 4 (200 mg, 0.58 mmol) was dissolved in DMF (3 mL) and NMM (160 μL, 1.46 mmol), EDC·HCl (246 mg, 1.28 mmol), HOBt (197 mg, 1.46 mmol) and methylamine (0.87 mL, 2 M in THF, 1.75 mmol) were added. The reaction mixture was stirred at room temperature for 3 d. The solvents were removed in vacuo. The residue was partitioned between EtOAc (50 mL) and sat aq NaHCO$_3$ solution (50 mL). The organic layer was washed with sat aq NaHCO$_3$ solution (2×50 mL), dried (MgSO$_4$) and the solvents were removed in vacuo. The residue was purified by reverse phase HPLC (YMC ODS-A 100×20 mm, 5 μm, 25 mL/min, gradient 30% to 90% (over 7 min) then 100% (3 min) MeOH in 10% MeOH/water) and reverse phase HPLC (YMC ODS-A 100×20 mm, 5 μm, 25 mL/min, gradient 40% to 80% (over 7 min) then 100% (3 min) MeOH in 10% MeOH/water) to give benzyl (4S,6S)-4-isopropyl-6-[(methylamino)carbonyl]-1,4,6,7-tetrahydro-5H-imidazo[4,5-c]pyridine-5-carboxylate (5 mg, 2.41%) as a white solid.

Analytical HPLC: purity 98.4% (System B, R$_T$=4.40 min); Analytical LCMS: purity 100% (System B, R$_T$=4.37 min), ES$^+$: 357.7 [MH]$^+$; HRMS calcd for C$_{19}$H$_{24}$N$_4$O$_3$: 356.1848, found 356.1843.

Example 13

5-Benzyl 6-methyl (4S,6S)-4-isopropyl-1,4,6,7-tetrahydro-5H-imidazo[4,5-c]pyridine-5,6-dicarboxylate

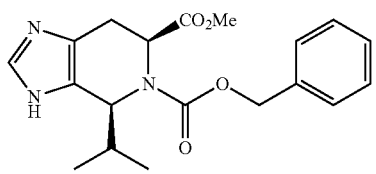

Intermediate 3 (1.00 g, 4.80 mmol) was dissolved in MeOH (10 mL) and conc. HCl (10 mL) was added. The reaction mixture was heated at 85° C. for 4 h. The solvents were removed in vacuo to give methyl (6S)-4-isopropyl-4,5,6,7-tetrahydro-1H-imidazo[4,5-c]pyridine-6-carboxylate dihydrochloride (mixture of 4S and 4R diastereomers; 1.42 g, crude, 100%).

Analytical LCMS: purity 88% (System A, R$_T$=0.51 min), ES$^+$: 224.54 [MH]$^+$.

Methyl (6S)-4-isopropyl-4,5,6,7-tetrahydro-1H-imidazo[4,5-c]pyridine-6-carboxylate dihydrochloride (mixture of 4S and 4R diastereomers; 1.42 g, 4.80 mmol) and DIPEA (4.18 mL, 24.0 mmol) were dissolved in THF (20 mL), the reaction mixture was cooled to 0° C. and benzyl chloroformate (1.37 mL, 9.60 mmol) was added. The reaction mixture was warmed to room temperature over 16 h. The reaction mixture was filtered and the filtrate was concentrated in vacuo to give a 2:1 mixture of 3,5-dibenzyl 6-methyl (6S)-4-isopropyl-6,7-dihydro-3H-imidazo[4,5-c]pyridine-3,5,6(4H)-tricarboxylate and 5-benzyl 6-methyl (6S)-4-isopropyl-1,4,6,7-tetrahydro-5H-imidazo[4,5-c]pyridine-5,6-dicarboxylate (mixture of 4S and 4R diastereomers; 3.05 g, crude).

Analytical LCMS: purity 23% (System A, R$_T$=1.65 min), ES$^+$: 358.5 and 66% (R$_T$=2.24 min), ES$^+$: 492.6.

A 2:1 mixture of 3,5-dibenzyl 6-methyl (6S)-4-isopropyl-6,7-dihydro-3H-imidazo[4,5-c]-pyridine-3,5,6(4H)-tricarboxylate and 5-benzyl 6-methyl (6S)-4-isopropyl-1,4,6,7-tetrahydro-5H-imidazo[4,5-c]pyridine-5,6-dicarboxylate (mixture of 4S and 4R diastereomers; 600 mg, ~1.20 mmol) was dissolved in DMF (6 mL) and methylamine (1.22 mL, 2 M in THF, 2.44 mmol) was added. The reaction mixture was split into 3 equal portions. The first reaction mixture was stirred at room temperature for 18 h. The second reaction mixture was heated at 60° C. for 4 h, methylamine (0.20 mL, 2 M in THF, 0.41 mmol) was added and the reaction mixture was heated under reflux at 80° C. for 18 h. The third reaction mixture was heated using a Biotage microwave (100° C., absorption high, pre-stirring 20 sec) for 20 min, methylamine (0.20 mL, 2 M in THF, 0.41 mmol) was added and the reaction mixture was heated using a Biotage microwave (120° C., absorption high, pre-stirring 20 sec) for 20 min. Methylamine (1.00 mL, 2 M in THF, 2.00 mmol) was added and the reaction mixture was heated using a Biotage microwave (160° C., absorption high, pre-stirring 20 sec) for 20 min. The 3 reaction mixtures were combined and the solvents were removed in vacuo. The residue was partitioned between EtOAc (30 mL) and sat aq NaHCO$_3$ solution (30 mL). The organic layer was washed with sat aq NaHCO$_3$ solution (30 mL), brine (30 mL), dried (MgSO$_4$) and the solvents were removed in vacuo. The residue was purified by column chromatography (normal phase, 20 g, Strata SI-1, silica gigatube, DCM (200 mL) followed by 2%, 4% and 5% MeOH in DCM (200 mL each)) and by reverse phase HPLC (YMC ODS-A 100×20 mm, 5 μm, 25 mL/min, gradient 40% to 90% (over 7 min) then 100% (3 min) MeOH in 10% MeOH/water) to give 5-benzyl 6-methyl (4S,6S)-4-isopropyl-1,4,6,7-tetrahydro-5H-imidazo[4,5-c]pyridine-5,6-dicarboxylate (46.2 mg, 2.7%) as a white solid.

Analytical HPLC: purity 99.7% (System B, R$_T$=4.93 min); Analytical LCMS: purity 100% (System B, R$_T$=4.86 min), ES$^+$: 358.6 [MH]$^+$; HRMS calculated for C$_{19}$H$_{23}$N$_3$O$_4$: 357.1689, found 357.1687.

Example 14

2-Phenoxyethyl 4-isopropyl-1,4,6,7-tetrahydro-5H-imidazo[4,5-c]pyridine-5-carboxylate

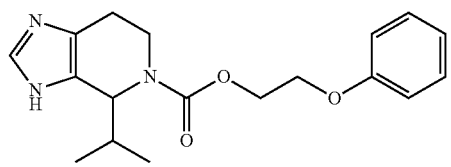 [SMILES: CC(C)C1c2[nH]cnc2CCN1C(=O)OCCOc1ccccc1]

2-Phenoxy-ethanol (500 mg, 3.60 mmol) and NMM (0.36 g, 0.35 mL, 3.60 mmol) were suspended in DCM (10 mL), cooled to 0° C. and 4-nitrophenyl chloroformate (0.72 g, 3.60 mmol) was added. The reaction mixture was stirred at room temperature for 2 h. A solution of Intermediate 1 (900 mg, 1.47 mol, 33% pure) and DIPEA (940 µL, 5.40 mmol) in DCM (20 mL) was added and the resulting solution was stirred at room temperature for 15 h, washed with 1 M aq $Na_2CO_3$ solution (6×100 mL), dried ($MgSO_4$) and the solvents were removed in vacuo. The residue was dissolved in MeOH (8 mL) and 1M aq NaOH solution (6 mL) and the reaction mixture was stirred at room temperature for 2 h then concentrated in vacuo. The residue was dissolved in EtOAc (100 mL) and the organic layer was washed with 1 M aq $Na_2CO_3$ solution (2×100 mL), brine (2×100 mL), dried ($MgSO_4$) and the solvents removed in vacuo. The residue was purified by reverse phase HPLC (YMC ODS-A 100×20 mm, 5 m, 25 mL/min, gradient 30% to 50% (over 7 min) then 100% (3 min) MeOH in 10% MeOH/water) and reverse phase HPLC (YMC ODS-A 100×20 mm, 5 µm, 25 mL/min, gradient 50% to 70% (over 7 min) then 100% (3 min) MeOH in 10% MeOH/water) to give 2-phenoxyethyl 4-isopropyl-1,4,6,7-tetrahydro-5H-imidazo[4,5-c]pyridine-5-carboxylate (27.2 mg, 5.6%) as a white gum.

Analytical HPLC: purity 100% (System B, $R_T$=4.79 min); Analytical LCMS: purity 100% (System B, $R_T$=5.17 min), $ES^+$: 330.1 $[MH]^+$; HRMS calculated for $C_{18}H_{23}N_3O_3$: 329.1739, found 329.1729.

Example 15

2-(4-Chlorophenoxy)ethyl 4-isopropyl-1,4,6,7-tetrahydro-5H-imidazo[4,5-c]pyridine-5-carboxylate

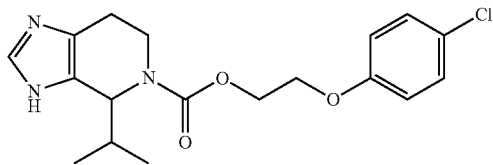 [SMILES: CC(C)C1c2[nH]cnc2CCN1C(=O)OCCOc1ccc(Cl)cc1]

2-(p-Chlorophenoxy)ethanol (0.73 g, 4.20 mmol) and NMM (0.55 mL, 5.70 mmol) were dissolved in DCM (10 mL), cooled to 0° C. and 4-nitrophenyl chloroformate (1.15 g, 5.70 mmol) was added. The reaction mixture was stirred at room temperature for 5 h. A solution of Intermediate 1 (0.70 g, 1.74 mmol, 50% pure) and DIPEA (1.48 mL, 8.50 mmol) in DCM (20 mL) was added and the resulting solution was stirred at room temperature for 2 d. The solvents were removed in vacuo, the residue was dissolved in MeOH (8 mL) and 1 M aq NaOH solution (6 mL) and the reaction mixture was stirred at room temperature for 3 h then concentrated in vacuo. The residue was dissolved in EtOAc (100 mL), washed with 1 M aq $Na_2CO_3$ solution (6×100 mL), dried ($MgSO_4$) and the solvents were removed in vacuo. The residue was purified reverse phase HPLC (YMC ODS-A 100×20 mm, 5 µm, 25 mL/min, gradient 70 to 100% (over 7 min) then 100% (3 min) MeOH in 10% MeOH/water) to give 2-(4-chlorophenoxy)ethyl 4-isopropyl-1,4,6,7-tetrahydro-5H-imidazo[4,5-c]pyridine-5-carboxylate (40.0 mg, 6.3%) as a white solid.

Analytical HPLC: purity 99.7% (System B, $R_T$=5.21 min); Analytical LCMS: purity 100% (System B, $R_T$=5.54 min), $ES^+$: 364.0 $[MH^{35}Cl]^+$ and 366.0 $[MH^{37}C_1]^+$; HRMS calculated for $C_{18}H_{22}ClN_3O_3$: 363.1350, found 363.1350.

Example 16

(3S)-Tetrahydrofuran-3-yl (4S)-4-isopropyl-1,4,6,7-tetrahydro-5H-imidazo[4,5-c]-pyridine-5-carboxylate

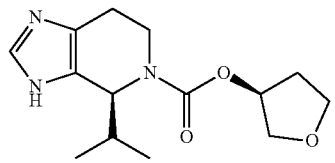 [SMILES: CC(C)[C@H]1c2[nH]cnc2CCN1C(=O)O[C@H]1CCOC1]

NaH (0.40 g, 10.0 mmol, 60% dispersion in mineral oil) was suspended in anhydrous THF (20 mL), cooled to 0° C. and (S)-3-hydroxytetrahydrofuran (0.88 g, 0.68 mL, 10.0 mmol) was added. The suspension was stirred at 0° C. for 30 min then added to a solution of Intermediate 2 (3.30 g, 10.0 mmol. 70% pure) in THF (60 mL) and the reaction mixture was stirred at room temperature. Two additional such portions of NaH and (S)-3-hydroxytetrahydrofuran in THF were added after 5 and 29 h, respectively. After 2 d the reaction mixture was quenched with water (10 mL) and the solvents were removed in vacuo. The residue was dissolved in EtOAc (100 mL), washed with 1 M aq $Na_2CO_3$ solution (4×100 mL), dried ($MgSO_4$) and the solvents were removed in vacuo. The residue was purified by column chromatography (normal phase, 20 g, Strata SI-1, silica gigatube, DCM (200 mL) followed by 2%, 4% and 5% MeOH in DCM (200 mL each)) and reverse phase HPLC (YMC ODS-A 100×20 mm, 5 µm, 25 mL/min, gradient 30% to 60% (over 7 min) then 100% (3 min) MeOH in 10% MeOH/water) to give (3S)-tetrahydrofuran-3-yl 4-isopropyl-1,4,6,7-tetrahydro-5H-imidazo[4,5-c]pyridine-5-carboxylate (34.8 mg, 1.1%) as a white solid.

Analytical HPLC: purity 100% (System B, $R_T$=3.63 min); Analytical LCMS: purity 100% (System B, $R_T$=4.01 min), $ES^+$: 280.1 $[MH]^+$.

(3S)-Tetrahydrofuran-3-yl-4-isopropyl-1,4,6,7-tetrahydro-5H-imidazo[4,5-c]pyridine-5-carboxylate (39.91 mg) was dissolved in 10 mM ammonium formate buffer and MeOH (2 mL, 1:1) and purified twice by reverse phase chiral HPLC (Chirobiotic T 250×10 mm, 3 mL/min, isocratic run 70% MeOH in 10 mM ammonium formate buffer (40 min), pH 7.4) to give a single diastereoisomer assigned as (3S)-tetrahydrofuran-3-yl (4S)-4-isopropyl-1,4,6,7-tetrahydro-5H-imidazo[4,5-c]pyridine-5-carboxylate (6.90 mg, 99% ee).

Analytical HPLC: purity 100% (System B, $R_T$=3.63 min); Chiral HPLC: purity 99.5% (System C, $R_T$=2.22 min); Analytical LCMS: purity 100% (System B, $R_T$=3.90 min), $ES^+$: 280.1 $[MH]^+$; HRMS calculated for $C_{14}H_{21}N_3O_3$: 279.1583, found 279.1571.

Example 17

Tetrahydrofuran-3-ylmethyl 4-isopropyl-1,4,6,7-tetrahydro-5H-imidazo[4,5-c]pyridine-5-carboxylate

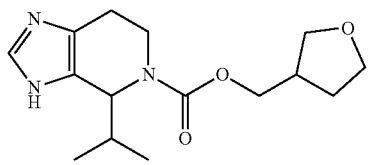 [SMILES: CC(C)C1c2[nH]cnc2CCN1C(=O)OCC1CCOC1]

Tetrahydro-3-furan-methanol (0.61 mL, 6.40 mmol) and NMM (0.64 g, 0.70 mL, 6.40 mmol) were dissolved in DCM (10 mL) at 0° C. and 4-nitrophenyl chloroformate (1.28 g, 6.40 mmol) was added. The reaction mixture was stirred at room temperature for 5 h. A solution of Intermediate 1 (0.50 g, 2.48 mmol) in DCM (20 mL) and DIPEA (2.11 mL, 12.1 mmol) was added to the reaction mixture and the resulting solution was stirred at room temperature for 18 h. The solvents were removed in vacuo, the residue was dissolved in MeOH (10 mL) and 1 M aq NaOH solution (10 mL) and the reaction mixture was stirred at room temperature for 2 h and concentrated in vacuo. The residue was dissolved in EtOAc (120 mL) and the organic layer was washed with 1 M aq $Na_2CO_3$ solution (4×100 mL), dried ($MgSO_4$) and the solvents were removed in vacuo. The residue was purified by column chromatography (normal phase, 20 g, Strata SI-1, silica gigatube, DCM (200 mL)) followed by 2%, 4%, 5% and 10% MeOH in DCM (200 mL each)) and reverse phase HPLC (YMC ODS-A 100×20 mm, 5 µm, 25 mL/min, gradient 20% to 100% (over 7 min) then 100% (3 min) MeOH in 10% MeOH/water and YMC ODS-A 100×20 mm, 5 µm, 25 mL/min, gradient 20% to 80% (over 7 min) then 100% (3 min) MeOH in 10% MeOH/water) to give tetrahydrofuran-3-ylmethyl 4-isopropyl-1,4,6,7-tetrahydro-5H-imidazo[4,5-c]pyridine-5-carboxylate (37.8 mg, 5.2%) as a white solid.

Analytical HPLC: purity 100% (System B, $R_T$=3.83 min); Analytical LCMS: purity 100% (System B, $R_T$=3.89 min), $ES^+$: 294.7 $[MH]^+$; HRMS calculated for $C_{15}H_{23}N_3O_3$: 293.1739, found 293.1744.

Example 18

(3-Methyloxetan-3-yl)methyl 4-isopropyl-1,4,6,7-tetrahydro-5H-imidazo[4,5-c]pyridine-5-carboxylate

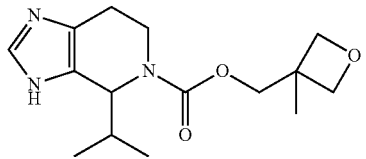 [SMILES: CC(C)C1c2[nH]cnc2CCN1C(=O)OCC1(C)COC1]

NaH (0.19 g, 4.80 mmol, 60% dispersion in mineral oil) was suspended in anhydrous THF (10 mL), cooled to 0° C. and 3-methyl-3-oxetane methanol (0.41 g, 4.00 mmol) was added. The suspension was stirred at 0° C. for 30 min then added to a solution of Intermediate 2 (1.33 g, 4.00 mmol, 70% pure) in THF (10 mL) and the reaction mixture was stirred at room temperature. Two additional such portions of NaH and 3-methyl-3-oxetane methanol in THF were added after 8 and 32 h, respectively. After 50 h the reaction mixture was quenched with water (10 mL) and the solvents were removed in vacuo. The residue was dissolved in EtOAc (100 mL) washed with 1 M aq $Na_2CO_3$ solution (4×100 mL), dried ($MgSO_4$) and the solvents were removed in vacuo. The residue was purified by column chromatography (normal phase, 20 g, Strata SI-1, silica gigatube, DCM (200 mL) followed by 2%, 4%, 5%. 10% and 20% MeOH in DCM (200 mL each)) and by reverse phase HPLC (YMC ODS-A 100×20 mm, 5 µm, 25 mL/min, gradient 20% to 100% (over 7 min) then 100% (3 min) MeOH in 10% MeOH/water) to give (3-methyloxetan-3-yl)methyl 4-isopropyl-1,4,6,7-tetrahydro-5H-imidazo[4,5-c]pyridine-5-carboxylate (68.2 mg, 5.8%) as a white solid.

Analytical HPLC: purity 100% (System B, $R_T$=3.80 min); Analytical LCMS: purity 100% (System B, $R_T$=4.08 min), $ES^+$: 294.1 $[MH]^+$; HRMS calculated for $C_{15}H_{23}N_3O_3$: 293.1739. found 293.1740.

Example 19

2-(Dimethylamino)ethyl 4-isopropyl-1,4,6,7-tetrahydro-5H-imidazo[4,5-c]pyridine-5-carboxylate

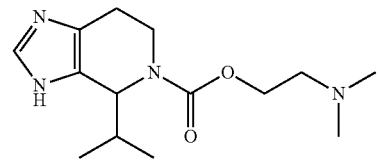 [SMILES: CC(C)C1c2[nH]cnc2CCN1C(=O)OCCN(C)C]

N,N-Dimethylethanolamine (1.46 mL, 14.5 mmol) was dissolved in DCM (10 mL) at 0° C. and NMM (1.40 mL, 14.5 mmol) and 4-nitrophenyl chloroformate (2.93 g, 13.5 mmol) were added. The reaction mixture was stirred at room temperature for 5 h. A solution of Intermediate 1 (2.36 g, 3.6 mmol) and DIPEA (2.53 mL, 14.5 mmol) in DCM (20 mL) was added and the resulting solution was stirred for 2 d. The solvents were removed in vacuo, the residue was dissolved in MeOH (8 mL) and 1 M aq NaOH solution (6 mL) and the reaction mixture was stirred for 18 h and concentrated in vacuo. The residue was dissolved in EtOAc (100 mL) and the organic layer was washed with 1 M aq $Na_2CO_3$ solution (6×100 mL), dried ($MgSO_4$) and concentrated in vacuo. The residue was purified by column chromatography (normal phase, 20 g, Strata SI-1, silica gigatube, DCM (200 mL) followed by 2% and 4% MeOH in DCM (200 mL each)) and reverse phase HPLC (YMC ODS-A 100×20 mm, 5 m, 25 mL per min, gradient 40% to 80% (over 7 min) then 100% (3 min) MeOH in 10% MeOH/water) to give 2-(dimethylamino)ethyl 4-isopropyl-1,4,6,7-tetrahydro-5H-imidazo[4,5-c]pyridine-5-carboxylate (7 mg, 0.7%) as a colourless gum.

Analytical HPLC: purity 98.6% (System B, $R_T$=2.90 min); Analytical LCMS: purity 100% (System B, $R_T$=2.81 min), $ES^+$: 281.8 $[MH]^+$; HRMS calculated for $C_{14}H_{24}N_4O_2$: 280.1899, found 280.1905.

Example 20

(2R)-Tetrahydrofuran-2-ylmethyl 4-isopropyl-1,4,6,7-tetrahydro-5H-imidazo[4,5-c]-pyridine-5-carboxylate

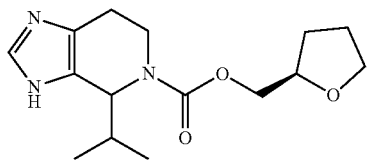 [SMILES: CC(C)C1c2[nH]cnc2CCN1C(=O)OC[C@H]1CCCO1]

(R)-tetrahydrofurfuryl alcohol (1.00 g, 9.80 mmol) was dissolved in DCM (10 mL) at 0° C. and NMM (0.99 g, 0.94 mL, 9.80 mmol) and 4-nitrophenyl chloroformate (1.97 g, 9.80 mmol) were added. The reaction mixture was stirred at room temperature for 5 h. A solution of Intermediate 1 (1.87 g, 3.6 mmol) and DIPEA (2.53 mL, 14.5 mmol) in DCM (20 mL) was added and the resulting solution was stirred for 2 d. The solvents were removed in vacuo, and the residue was dissolved in MeOH (8 mL) and 1 M aq NaOH solution (6 mL) and the reaction mixture was stirred for 18 h and concentrated in vacuo. The residue was dissolved in EtOAc (100 mL) and the organic layer was washed with 1 M aq $Na_2CO_3$ solution (6×100 mL), dried ($MgSO_4$) and concentrated in vacuo. The residue was purified by reverse phase column chromatography (LiChroprep RP-18, 40-63 μm, 460×26 mm (100 g), 30 mL per min, gradient 0% to 20% (over 5 min) to 90% (over 40 min) MeOH in water) and reverse phase HPLC (YMC ODS-A 150×20 mm, 5 μm, 15 mL per min, gradient 50% to 65% (over 12 min) then 100% (3 min) MeOH in 10% MeOH/water) to give (2R)-tetrahydrofuran-2-ylmethyl 4-isopropyl-1,4,6,7-tetrahydro-5H-imidazo[4,5-c]pyridine-5-carboxylate (46.7 mg, 4.4%) as a colourless gum.

Analytical HPLC: purity 99.4% (System B, $R_T$=3.75 min); Analytical LCMS: purity 100% (System B, $R_T$=4.29 min), ES$^+$: 294.1 [MH]$^+$; HRMS calculated for $C_{15}H_{23}N_3O_3$: 293.1739. found 293.1738.

Example 21

1,3-Thiazol-2-ylmethyl 4-isopropyl-1,4,6,7-tetrahydro-5H-imidazo[4,5-c]pyridine-5-carboxylate

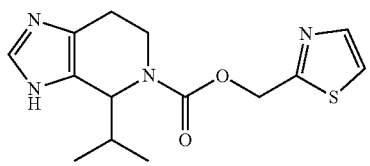 [SMILES: CC(C)C1c2[nH]cnc2CCN1C(=O)OCc1nccs1]

2-Hydroxymethylthiazole (0.97 g, 8.40 mmol) was dissolved in DCM (10 mL) at 0° C. and NMM (0.85 g, 0.81 mL, 8.40 mmol) and 4-nitrophenyl chloroformate (1.70 g, 8.40 mmol) were added. The reaction mixture was stirred at room temperature for 5 h. A solution of Intermediate 1 (2.18 g, 4.20 mmol) and DIPEA (1.64 g, 2.21 mL, 12.7 mmol) in DCM (20 mL) was added and the resulting solution was stirred for 19 h. The solvents were removed in vacuo, the residue was dissolved in MeOH (8 mL) and 1 M aq NaOH solution (6 mL) and the reaction mixture was stirred at room temperature for 3 d and concentrated in vacuo. The residue was dissolved in EtOAc (100 mL) and the organic layer was washed with 1 M aq $Na_2CO_3$ solution (6×100 mL), dried ($MgSO_4$) and concentrated in vacuo. The residue was purified by column chromatography (normal phase, 20 g, Strata SI-1, silica gigatube, DCM (200 mL) followed by 2% and 4% MeOH in DCM (200 mL each)) and reverse phase HPLC (YMC ODS-A 150×20 mm, 5 μm, 25 mL per min, gradient 20% to 80% (over 12 min) then 100% (3 min) MeOH in 10% MeOH/water) to give 1,3-thiazol-2-ylmethyl 4-isopropyl-1,4,6,7-tetrahydro-5H-imidazo[4,5-c]pyridine-5-carboxylate (51.8 mg, 4.0%) as a white solid.

Analytical HPLC: purity 99.5% (System B, $R_T$=3.81 min); Analytical LCMS: purity 100% (System B, $R_T$=4.27 min), ES$^+$: 307.1 [MH]$^+$; HRMS calculated for $C_{14}H_{18}N_4O_2S$: 306.1150, found 306.1153.

Example 22

(5-Methylisoxazol-3-yl)methyl 4-isopropyl-1,4,6,7-tetrahydro-5H-imidazo[4,5-c]-pyridine-5-carboxylate

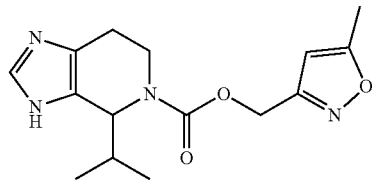 [SMILES: Cc1cc(COC(=O)N2CCc3nc[nH]c3C2C(C)C)no1]

5-Methylisoxazole-3-methanol (1.64 g, 14.5 mmol) was dissolved in DCM (10 mL) at 0° C. and NMM (1.47 g, 1.40 mL, 14.5 mmol) and 4-nitrophenyl chloroformate (2.93 g, 14.5 mmol) were added. The reaction mixture was stirred at room temperature for 18 h. A solution of Intermediate 1 (1.87 g, 3.60 mmol) in DCM (20 mL) and DIPEA (1.87 g, 2.52 mL, 14.5 mmol) was added and the resulting solution was stirred for 3 d and concentrated in vacuo. The residue was dissolved in MeOH (8 mL) and 1 M aq NaOH solution (6 mL) and the reaction mixture was stirred for 18 h and concentrated in vacuo. The residue was dissolved in EtOAc (100 mL) and the organic layer was washed with 1 M aq $Na_2CO_3$ solution (6×100 mL), dried ($MgSO_4$) and concentrated in vacuo. The residue was purified by reverse phase column chromatography (LiChroprep RP-18, 40-63 μm, 460×26 mm (100 g), 30 mL per min, gradient 0% to 20% (over 5 min) to 90% (over 40 min) MeOH in water) and reverse phase HPLC (YMC ODS-A 150×20 mm, 5 μm, 25 mL per min, gradient 40% to 80% (over 7 min) then 100% (3 min) MeOH in 10% MeOH/water) to give (5-methylisoxazol-3-yl)methyl 4-isopropyl-1,4,6,7-tetrahydro-5H-imidazo[4,5-c]pyridine-5-carboxylate (107 mg, 9.7%) as a colourless gum.

Analytical HPLC: purity 99.5% (System B, $R_T$=4.09 min); Analytical LCMS: purity 100% (System B, $R_T$=4.51 min), ES$^+$: 305.2 [MH]$^+$; HRMS calculated for $C_{15}H_{20}N_4O_3$: 304.1535, found 304.1538.

Example 23

[(2S)-1-Methylpyrrolidin-2-yl]methyl 4-isopropyl-1,4,6,7-tetrahydro-5H-imidazo[4,5-c]pyridine-5-carboxylate

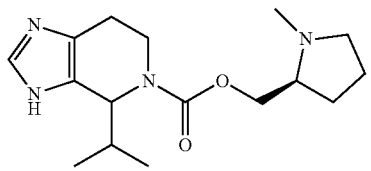 [SMILES: CC(C)C1c2[nH]cnc2CCN1C(=O)OC[C@@H]1CCCN1C]

NaH (0.19 g, 5.00 mmol, 60% dispersion in mineral oil) was suspended in THF (10 mL) at 0° C. and (S)—N-methylpyrrolidine-2-methanol (0.47 mL, 4.80 mmol) was added. The suspension was stirred at 0° C. for 30 min and added to a solution of Intermediate 2 (1.33 g, 4.00 mmol) in THF (10 mL) and the reaction mixture was stirred at room temperature. An additional such portion of NaH and N-methylpyrrolidine methanol in THF was added after 8 h. After 18 h the reaction mixture was quenched with water (10 mL) and the solvents were removed in vacuo. The residue was dissolved in EtOAc (100 mL), washed with 1 M aq $Na_2CO_3$ solution (4×100 mL), dried ($MgSO_4$) and the solvents were removed in vacuo. The residue was purified by column chromatography (normal phase, 20 g, Strata SI-1, silica gigatube, DCM (200 mL) followed by 2%, 4%, 5%, 10%, and 20% MeOH in DCM (200 mL)) and reverse phase HPLC (Phenomenex Synergi, RP-Hydro 150×10 mm, 10 μm, 15 mL per min, gradient 0% to 60% (over 12 min) to 100% (over 3 min) MeOH in water [1% formic acid]). The residue was de-salted using $K_2CO_3$ in DCM to give [(2S)-1-methylpyrrolidin-2-yl]methyl 4-isopropyl-1,4,6,7-tetrahydro-5H-imidazo[4,5-c]pyridine-5-carboxylate (52.1 mg, 4.2%) as a colourless gum.

Analytical HPLC: purity 100% (System B, $R_T$=3.09 min); Analytical LCMS: purity 100% (System B, $R_T$=3.44 min), ES$^+$: 307.1 [MH]$^+$; HRMS calculated for $C_{16}H_{26}N_4O_2$: 306.2056, found 306.2068.

Example 24

(3R)-1-methylpyrrolidin-3-yl 4-isopropyl-1,4,6,7-tetrahydro-5H-imidazo[4,5-c]pyridine-5-carboxylate

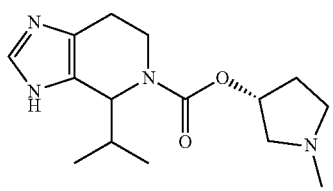 [SMILES: CC(C)C1c2[nH]cnc2CCN1C(=O)O[C@@H]1CCN(C)C1]

NaH (0.19 g, 5.00 mmol, 60% dispersion in mineral oil) was suspended in THF (10 mL) at 0° C. and (R)-1-methylpyrrolidin-3-ol (0.47 mL, 4.00 mmol) was added. The suspension was stirred at 0° C. for 30 min and added to a solution of Intermediate 2 (1.33 g, 4.00 mmol) in THF (10 mL) and the reaction mixture was stirred at room temperature. Two additional such portions of NaH and (R)-1-methylpyrrolidin-3-ol in THF were added after 18 and 26 h, respectively. After 44 h the reaction mixture was quenched with water (10 mL) and the solvents were removed in vacuo. The residue was dissolved in EtOAc (100 mL), washed with 1 M aq $Na_2CO_3$ solution (4×100 mL), dried ($MgSO_4$) and the solvents were removed in vacuo. The residue was purified by column chromatography (normal phase, 20 g, Strata SI-1, silica gigatube, DCM (200 ml) followed by 2%, 4%, 5%, 10% and 20% MeOH in DCM (200 mL)) and reverse phase HPLC (Phenomenex Synergi, RP-Hydro 150×10 mm, 10 μm, 15 mL per min, gradient 0% to 30% (over 12 min) to 100% (over 3 min) MeOH in water [1% formic acid]). The residue was de-salted using $K_2CO_3$ in DCM to give (3R)-1-methylpyrrolidin-3-yl 4-isopropyl-1,4,6,7-tetrahydro-5H-imidazo-[4,5-c]pyridine-5-carboxylate (32.3 mg, 2.7%) as a colourless gum.

Analytical HPLC: purity 100% (System B, $R_T$=2.99 min); Analytical LCMS: purity 100% (System B, $R_T$=3.36 min), ES$^+$: 293.1 [MH]$^+$; HRMS calculated for $C_{15}H_{24}N_4O_2$: 292.1899, found 292.1910.

Example 25

Oxetan-2-ylmethyl 4-isopropyl-1,4,6,7-tetrahydro-5H-imidazo[4,5-c]pyridine-5-carboxylate

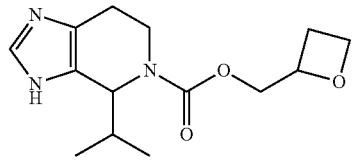 [SMILES: CC(C)C1c2[nH]cnc2CCN1C(=O)OCC1CCO1]

2-Hydroxymethyloxetane (0.71 g, 8.10 mmol) was dissolved in DCM (10 mL) at 0° C. and NMM (0.89 mL, 8.10 mmol) and 4-nitrophenyl chloroformate (1.63 g, 8.10 mmol) were added. The reaction mixture was stirred at room temperature for 5 h. A solution of Intermediate 1 (1.16 g, 3.90 mmol) and DIPEA (2.69 mL, 15.4 mmol) in DCM (20 mL) was added and the resulting solution was stirred for 18 h. The solvents were removed in vacuo, the residue was dissolved in MeOH (10 mL) and 1 M aq NaOH solution (10 mL) and the reaction mixture was stirred for 2 h and concentrated in vacuo. The residue was dissolved in EtOAc (120 mL), the organic layer was washed with 1M aq $Na_2CO_3$ solution (4×100 mL), dried ($MgSO_4$) and the solvents were removed in vacuo. The residue was purified by column chromatography (normal phase, 20 g, Strata SI-1, silica gigatube, DCM (200 ml) followed by 2%, 4% and 5% MeOH in DCM (200 mL)) and reverse phase HPLC (YMC ODS-A 100×20 mm, 5 μm, 25 mL per min, gradient 20% to 100% (over 7 min) then 100% (3 min) MeOH in 10% MeOH/water) to give oxetan-2-ylmethyl 4-isopropyl-1,4,6,7-tetrahydro-5H-imidazo[4,5-c]pyridine-5-carboxylate (93.4 mg, 8.7%) as a white solid.

Analytical HPLC: purity 100% (System B, $R_T$=3.58 min); Analytical LCMS: purity 100% (System B, $R_T$=3.84 min), ES$^+$: 280.1 [MH]$^+$; HRMS calculated for $C_{14}H_{21}N_3O_3$: 279.1583, found 279.1594.

Example 26

2-(Pyridin-3-yloxy)ethyl 4-isopropyl-1,4,6,7-tetrahydro-5H-imidazo[4,5-c]pyridine-5-carboxylate

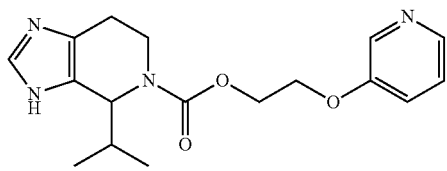 [SMILES: CC(C)C1c2[nH]cnc2CCN1C(=O)OCCOc1cccnc1]

2-(3-Pyridyloxy)ethanol (0.62 g, 4.40 mmol) was dissolved in DCM (10.0 mL) at 0° C. and NMM (0.50 mL, 4.40 mmol) and 4-nitrophenyl chloroformate (0.90 g, 4.40 mmol) were added. The reaction mixture was stirred at room temperature for 5 h. A solution of Intermediate 1 (0.35 g, 2.10 mmol) and DIPEA (1.10 g, 1.50 mL, 8.50 mmol) in DCM (20 mL) was added and the resulting solution was stirred for 3 d. The solvents were removed in vacuo, the residue was dissolved in MeOH (4 mL) and 1 M aq NaOH solution (4 mL) and the reaction mixture was stirred for 2 h and concentrated in vacuo. The residue was dissolved in EtOAc (60 mL), the organic layer was washed with 1 M aq Na$_2$CO$_3$ solution (5×40 mL), dried (MgSO$_4$) and the solvents were removed in vacuo. The residue was purified by column chromatography (normal phase, 20 g, Strata SI-1, silica gigatube, DCM (200 mL) followed by 2%, 4%, 5% and 10% MeOH in DCM (200 mL)) and reverse phase HPLC (YMC ODS-A 100×20 mm, 5 m, 25 mL per min, gradient 0% to 40% (over 7 min) then 100% (3 min) MeOH in 10% MeOH/water) to give 2-(pyridin-3-yloxy)ethyl 4-isopropyl-1,4,6,7-tetrahydro-5H-imidazo[4,5-c]pyridine-5-carboxylate (7.4 mg, 1%) as a white solid.

Analytical HPLC: purity 99.4% (System B, R$_T$=3.21 min); Analytical LCMS: purity 100% (System B, R$_T$=3.20 min), ES$^+$: 331.5 [MH]$^+$; HRMS calculated for C$_{17}$H$_{22}$N$_4$O$_3$: 330.1692, found 330.1701.

Example 27

2-(2,2,2-Trifluoroethoxy)ethyl 4-isopropyl-1,4,6,7-tetrahydro-5H-imidazo[4,5-c]-pyridine-5-carboxylate

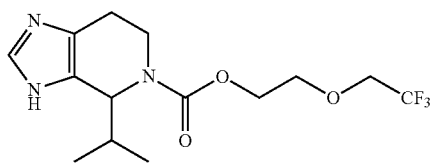 [SMILES: CC(C)C1c2[nH]cnc2CCN1C(=O)OCCOCC(F)(F)F]

2-(2,2,2-Trifluoroethoxy)ethanol (0.57 mL, 3.60 mmol) was dissolved in THF (5 mL), NaH (146 mg, 60% dispersion in mineral oil, 3.60 mmol) was added and the reaction mixture was stirred for 10 min. 4-Nitrophenyl chloroformate (726 mg, 3.60 mmol) was added and the reaction mixture was stirred for 16 h. Intermediate 1 (297 mg, 1.80 mmol) was dissolved in THF (5 mL) and added to the reaction mixture which was stirred at room temperature. Three additional such portions of NaH, 2-(2,2,2-trifluoroethoxy) ethanol and 4-nitrophenyl chloroformate in THF were added after 8, 24 and 32 h, respectively. After 104 h the reaction mixture was quenched with water (10 mL) and the solvents were removed in vacuo. The residue was dissolved in MeOH (10 mL) and 1 M aq NaOH solution (6 mL) and stirred for 1.5 h. The solvents were removed in vacuo and the residue dissolved in EtOAc (100 mL). The organic layer was washed with 1 M aq Na$_2$CO$_3$ solution (6×50 mL), brine (2×50 mL), dried (MgSO$_4$) and the solvents were removed in vacuo. The residue was purified by reverse phase HPLC (Phenomenex Synergi, RP-Hydro 150×10 mm, 10 µm, 15 mL per min, gradient 0% to 50% (over 12 min) to 100% (over 3 min) MeOH in water to give 2-(2,2,2-trifluoroethoxy)ethyl 4-isopropyl-1,4,6,7-tetrahydro-5H-imidazo[4,5-c]pyridine-5-carboxylate (3 mg, 0.5%) as a pale yellow gum.

Analytical HPLC: purity 99.3% (System B, R$_T$=4.49 min); Analytical LCMS: purity 97.1% (System B, R$_T$=4.50 min), ES$^+$: 336.5 [MH]$^+$; HRMS calculated for C$_{14}$H$_{20}$F$_3$N$_3$O$_3$: 335.1457, found 335.1467.

Biological Tests

Biological Assay of the SSAO Enzyme Inhibitors

All assays were performed in room temperature with purified recombinantly expressed human SSAO. Enzyme was prepared essentially as described in Öhman et al. (*Protein Expression and Purification* 2006, 46, 321-331). The enzyme activity was measured with benzylamine as substrate and utilized the production of hydrogen peroxide for detection. In a horseradish peroxidise (HRP) coupled reaction, hydrogen peroxide oxidation of 10-acetyl-3,7-dihydroxyphenoxazine produced resorufin, which is a highly fluorescent compound (Zhout and Panchuk-Voloshina. *Analytical Biochemistry* 1997, 253, 169-174; Amplex® Red Hydrogen Peroxide/peroxidise Assay kit, Invitrogen A22188).

Briefly, test compounds were dissolved in dimethyl sulfoxide (DMSO) to a concentration of 10 mM. Dose-response measurements were assayed by either creating 1:10 serial dilutions in DMSO to produce a 7 point curve or by making 1:3 serial dilutions in DMSO to produce 11 point curves. The top concentrations were adjusted depending on the potency of the compounds and subsequent dilution in reaction buffer (50 mM sodium phosphate, pH 7.4) yielded a final DMSO concentration≤2%. Enzyme and compounds were set to pre-incubate in flat-bottomed microtiter plates for approximately 60 minutes before initiating the reaction by addition of a mixture of HRP, benzylamine and Amplex reagent. Fluorescence intensity was then measured at several time points (15 minutes, 20 minutes and 30 minutes) exciting at 544 nm and reading the emission at 590 nm). Final concentrations of the reagents in the assay wells were: SSAO enzyme 2 µg/ml, benzylamine 100 µM, Amplex reagent 20 µM, HRP 0.1 U/mL and varying concentrations of test compound. The inhibition was measured as % decrease of the signal compared to a control without inhibitor (only diluted DMSO). The background signal from a sample containing no SSAO enzyme was subtracted from all data points. Data was fitted to a four parameter logistic model and IC$_{50}$ values were calculated using the GraphPad Prism 4 or XLfit 4 programs.

The exemplified compounds of the invention generally had an IC$_{50}$ value of 1-1000 nM. Obtained IC$_{50}$ values for representative compounds are shown in the table below:

| Compound | IC$_{50}$ (nM) |
|---|---|
| Example 7 | 34 |
| Example 14 | 48 |
| Example 17 | 91 |

The invention claimed is:

1. A method of synthesizing a compound of formula (I):

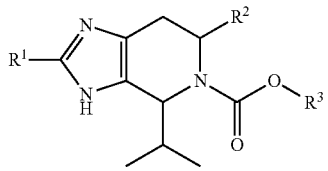
(I)

or a pharmaceutically acceptable salt, solvate, hydrate, geometrical isomer, tautomer, optical isomer, or N-oxide thereof, wherein:

$R^1$ is selected from:
 (a) hydrogen,
 (b) $C_{1-6}$-alkyl, and
 (c) —$NR^{4A}R^{4B}$;

$R^2$ is selected from:
 (a) hydrogen,
 (b) —C(O)OMe,
 (c) —C(O)NH2, and
 (d) —C(O)NHMe;

$R^3$ is selected from:
 (a) $C_{1-6}$-alkyl,
 (b) halo-$C_{1-6}$-alkyl,
 (c) hydroxy-$C_{1-6}$-alkyl,
 (d) $C_{1-6}$-alkoxy-$C_{1-6}$-alkyl,
 (e) halo-$C_{1-6}$-alkoxy-$C_{1-6}$-alkyl,
 (f) $N(R^{4A}R^{4B})$—$C_{1-6}$-alkyl,
 (g) $C_{6-10}$-aryl-$C_{1-4}$-alkyl,
 (h) heteroaryl-$C_{1-4}$-alkyl,
 (i) $C_{6-10}$-aryloxy-$C_{1-4}$-alkyl,
 (j) heteroaryloxy-$C_{1-4}$-alkyl,
 (k) $C_{3-8}$-cycloalkyl,
 (l) $C_{3-8}$-cycloalkyl-$C_{1-4}$-alkyl,
 (m) heterocyclyl, and
 (n) heterocyclyl-$C_{1-4}$-alkyl, wherein any aryl or heteroaryl residue is optionally substituted with one or more substituents independently selected from halogen, hydroxy, cyano, nitro, $CF_3$, $C_{1-4}$-alkyl, $C_{1-4}$-alkoxy, and —$NR^{4A}R^{4B}$, and wherein any cycloalkyl or heterocyclyl residue is optionally substituted with one or more substituents independently selected from halogen, hydroxy, $C_{1-4}$-alkyl, $C_{1-4}$-alkoxy and —$NR^{4A}R^{4B}$; and $R^{4A}$ and $R^{4B}$ are each independently selected from:
 (a) hydrogen,
 (b) $C_{1-6}$-alkyl, and
 (c) $C_{1-6}$-acyl;

provided that when $R^1$ and $R^2$ are hydrogen, then $R^3$ is not benzyl;

the method comprising:
 reacting together a compound of formula (III) with a compound of formula (IV):

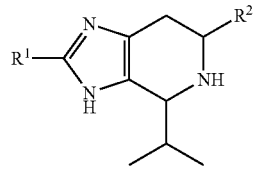
(III)

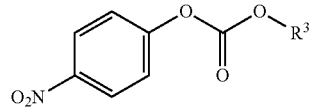
(IV)

where $R^1$, $R^2$, and $R^3$ are as defined in formula (I), in the presence of a base to obtain the compound of formula (I); or reacting a compound of formula (III) with 4-nitrophenyl chloroformate to form a compound of formula (V):

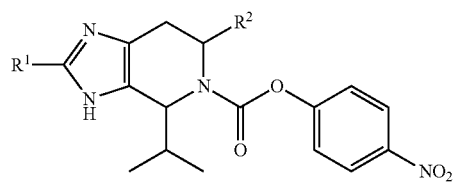
(V)

where $R^1$ and $R^2$ are as defined in formula (I); and reacting the compound of formula (V) with $R^3$OH, where $R^3$ is as defined in formula (I), to obtain the compound of formula (I).

2. The method according to claim 1, wherein $R^1$ is H.

3. The method according to claim 1, wherein $R^3$ is selected from halo-$C_{1-2}$-alkyl, halo-$C_{1-2}$-alkoxy-$C_{1-2}$-alkyl, di($C_{1-2}$-alkyl)amino-$C_{1-2}$-alkyl, phenyl-$C_{1-2}$-alkyl, phenoxy-$C_{1-2}$-alkyl, $C_{5-6}$-heteroaryl-$C_{1-2}$-alkyl, $C_{5-6}$-heteroaryloxy-$C_{1-2}$-alkyl, heterocyclyl and heterocyclyl-$C_{1-2}$-alkyl, and wherein any phenyl, heteroaryl or heterocyclyl residue is optionally substituted with one or two substituents independently selected from halogen and $C_{1-2}$-alkyl.

4. A method of synthesizing a compound of formula (I):

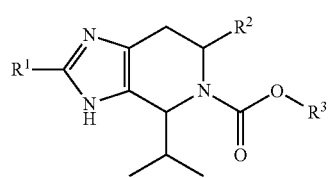
(I)

or a pharmaceutically acceptable salt, solvate, hydrate, geometrical isomer, tautomer, optical isomer, or N-oxide thereof, wherein:

$R^1$ is selected from:
 (a) hydrogen,
 (b) $C_{1-6}$-alkyl, and
 (c) —$NR^{4A}R^{4B}$;

$R^2$ is selected from:
 (a) hydrogen,
 (b) —C(O)OMe,
 (c) —C(O)NH2, and
 (d) —C(O)NHMe;

$R^3$ is selected from:
(a) halo-$C_{1-4}$-alkyl,
(b) halo-$C_{1-4}$-alkoxy-$C_{1-4}$-alkyl
(c) di($C_{1-4}$-alkyl)-amino-$C_{1-4}$-alkyl,
(d) $C_{6-10}$-aryl-$C_{1-4}$-alkyl,
(e) $C_{6-10}$-aryloxy-$C_{1-4}$-alkyl,
(f) heteroaryl-$C_{1-4}$-alkyl,
(g) heteroaryloxy-$C_{1-4}$-alkyl, and
(h) heterocyclyl and heterocycly-$C_{1-4}$-alkyl,
wherein any aryl, heteroaryl or heterocyclyl residue is optionally substituted with one or two substituents independently selected from halogen and $C_{1-4}$-alkyl; and
$R^{4A}$ and $R^{4B}$ are each independently selected from:
(d) hydrogen,
(e) $C_{1-6}$-alkyl, and
(f) $C_{1-6}$-acyl;
provided that when $R^1$ and $R^2$ are hydrogen, then $R^3$ is not benzyl;
the method comprising:
reacting together a compound of formula (III) with a compound of formula (IV):

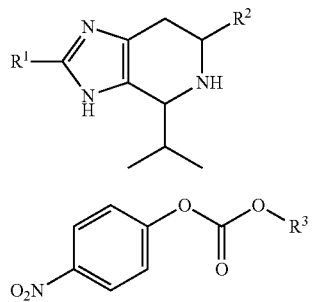

(III)

(IV)

where $R^1$, $R^2$, and $R^3$ are as defined in formula (I), in the presence of a base to obtain the compound of formula (I); or reacting a compound of formula (III) with 4-nitrophenyl chloroformate to form a compound of formula (V):

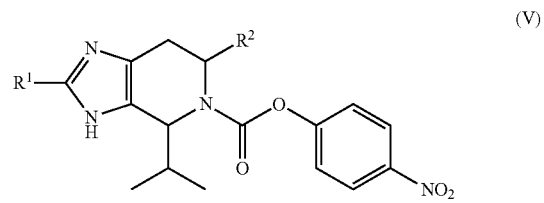

(V)

here $R^1$ and $R^2$ are as defined in formula (I); and reacting the compound of formula (V) with $R^3OH$, where $R^3$ is as defined in formula (I), to obtain the compound of formula (I).

5. The method according to claim 4, wherein $R^1$ is H.

6. The method according to claim 4, wherein $R^3$ is 2,2,2-trichloroethyl, 2-chloro-2,2-difluoroethyl, 2,2,2-trifluoroethoxyethyl, dimethylaminoethyl, benzyl, pyridinylmethyl, pyrazinylmethyl, thiazolylmethyl, isoxazolylmethyl, phenoxyethyl, pyridinyloxyethyl, tetrahydrofuranyl, tetrahydrofuranylmethyl, pyrrolidinyl, pyrrolidinylmethyl or oxetanylmethyl, wherein any phenyl, heteroaryl, or heterocyclyl residue is optionally monosubstituted with halogen or methyl.

* * * * *